(12) United States Patent
Hirschmann et al.

(10) Patent No.: US 6,544,602 B1
(45) Date of Patent: Apr. 8, 2003

(54) SUPERTWIST LIQUID-CRYSTAL DISPLAYS AND LIQUID-CRYSTAL MIXTURES THEREFOR

(75) Inventors: Harald Hirschmann, Darmstadt (DE); Clarissa Weller, Mörfelden/Walldorf (DE); Georg Weber, Erzhausen (DE); Kazuo Totani, Naka-gun (JP); Akihiro Kojima, Darmstadt (DE)

(73) Assignee: Merck Patent Gesellschaft mit beschränkter Haftung, Darmstadt (DE)

( * ) Notice: Subject to any disclaimer, the term of this patent is extended or adjusted under 35 U.S.C. 154(b) by 0 days.

(21) Appl. No.: 09/564,562

(22) Filed: May 4, 2000

(30) Foreign Application Priority Data

May 4, 1999 (DE) .......................... 199 20 405

(51) Int. Cl.$^7$ .................. C09K 19/30; C09K 19/34; C09K 19/12; G02F 1/133
(52) U.S. Cl. ............. 428/1.1; 252/299.61; 252/299.63; 252/299.66; 349/179; 349/186
(58) Field of Search .............. 252/299.63, 299.01, 252/299.66, 299.61; 428/1.1; 349/179, 186

(56) References Cited

U.S. PATENT DOCUMENTS

| | | | | |
|---|---|---|---|---|
| 5,679,285 A | * | 10/1997 | Bartmann et al. | 252/299.63 |
| 6,017,469 A | * | 1/2000 | Reiffenrath et al. | 252/299.63 |
| 6,174,572 B1 | * | 1/2001 | Hirschmann et al. | 428/1.1 |

* cited by examiner

*Primary Examiner*—Shean C. Wu
(74) *Attorney, Agent, or Firm*—Millen, White, Zelano & Branigan, P.C.

(57) ABSTRACT

The invention relates to supertwist liquid-crystal displays (SLCDs) having very short response times and good steepnesses and angle dependencies, and to the novel nematic liquid-crystal mixtures used therein, which are distinguished in that they comprise at least one compound of the formula IA

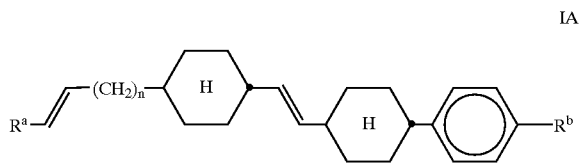

and at least one compound of the formula IB

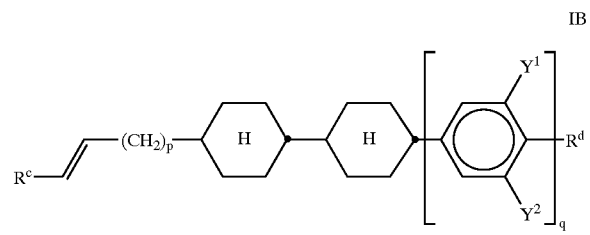

in which $R^a$, $R^b$, $R^c$, $R^d$, $Y^1$, $Y^2$, n and p have the meaning given.

29 Claims, No Drawings

SUPERTWIST LIQUID-CRYSTAL DISPLAYS AND LIQUID-CRYSTAL MIXTURES THEREFOR

The invention relates to supertwist liquid-crystal displays (SLCDs or supertwisted nematic (STN) displays) having very short response times and good steepnesses and angle dependencies, and to the novel nematic liquid-crystal mixtures used therein.

SLCDs are known, for example from EP 0 131 216 B1; DE 34 23 993 A1; EP 0 098 070 A2; M. Schadt and F. Leenhouts, 17th Freiburg Congress on Liquid Crystals (8.-10.04.87); K. Kawasaki et al., SID 87 Digest 391 (20.6); M. Schadt and F. Leenhouts, SID 87 Digest 372 (20.1); K. Katoh et al., Japanese Journal of Applied Physics, Vol. 26, No. 11, L 1784–L 1786 (1987); F. Leenhouts et al., Appl. Phys. Lett. 50 (21), 1468 (1987); H. A. van Sprang and H. G. Koopman, J. Appl. Phys. 62 (5), 1734 (1987); T. J. Scheffer and J. Nehring, Appl. Phys. Lett. 45 (10), 1021 (1984), M. Schadt and F. Leenhouts, Appl. Phys. Lett. 50 (5), 236 (1987), and E. P. Raynes, Mol. Cryst. Liq. Cryst. Letters Vol. 4 (1), pp. 1–8 (1986). The term SLCD here covers any relatively highly twisted display element with a value for the twist angle of between 160° and 360°, such as, for example, the display elements of Waters et al. (C. M. Waters et al., Proc. Soc. Inf. Disp. (New York) (1985) (3rd Intern. Display Conference, Kobe, Japan), STN-LCDs (DE-A 35 03 259), SBE-LCDs (T. J. Scheffer and J. Nehring, Appi. Phys. Lett. 45 (1984) 1021), OMI-LCDs (M. Schadt and F. Leenhouts, Appl. Phys. Lett. 50 (1987), 236, DST-LCDs (EP-A 0 246 842) or BW-STN-LCDs (K. Kawasaki et al., SID 87 Digest 391 (20.6)).

SLCDs of this type are distinguished, in comparison to standard TN displays, by significantly better steepnesses of the electro-optical characteristic line and consequently better contrast values, and by significantly lower angle dependence of the contrast. Of particular interest are SLCDs having very short response times, in particular also at relatively low temperatures. In order to achieve short response times, the rotational viscosities of the liquid-crystal mixtures have hitherto been optimized using usually monotropic additives having relatively high vapour pressure. However, the response times achieved were not adequate for all applications.

In order to achieve a steep electro-optical characteristic line in SLCDs, the liquid-crystal mixtures should have relatively large values for $K_3/K_1$ and relatively small values for $\Delta\epsilon/\epsilon_1$.

In addition to optimization of the contrast and the response times, further important requirements are made of mixtures of this type:

1. A broad d/p window
2. High long-term chemical stability
3. High electrical resistance
4. Low frequency and temperature dependence of the threshold voltage.

The parameter combinations achieved are still far from adequate, in particular for high-multiplex, but also for low- and medium-multiplex STNs (1/400). This is in some cases attributable to the fact that the various requirements are affected in opposite manners by material parameters.

There thus continues to be a great demand for SLCDs, in particular for high-resolution displays (XGAs), having very short response times and at the same time a large operating temperature range, high characteristic line steepness, good angle dependence of the contrast and low threshold voltage which meet the abovementioned requirements.

The invention has an object of providing SLCDs which do not have the abovementioned disadvantages, or only do so to a lesser extent, and at the same time have very good response times, in particular at low temperatures, and very good steepnesses.

Upon further study of the specification and appended claims, further objects and advantages of this invention will become apparent to those skilled in the art.

Particularly, it has been found that advantages are achieved if nematic liquid-crystal mixtures are used which comprise compounds of the formula IA

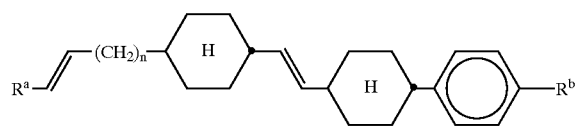

IA in combination with compounds of the formula IB

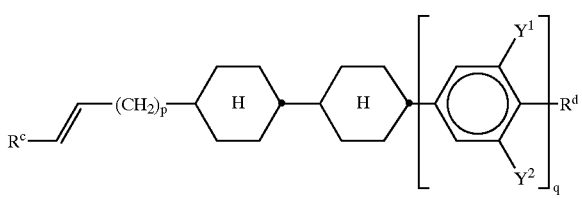

IB in which

| | |
|---|---|
| $R^a$ and $R^c$, | independently of one another, are H or an alkyl group having 1 to 7 carbon atoms, |
| $R^b$ | is an alkyl or alkoxy group having 1 to 10 carbon atoms or an alkenyl or alkenyloxy group having 2 to 10 carbon atoms, |
| $R^d$ | is F, $OCF_3$, $OCHF_2$, alkyl or alkoxy having 1 to 7 carbon atoms or alkenyl having 2 to 7 carbon atoms, |
| $Y^1$ and $Y^2$, | independently of one another, are H or F, |
| q | is 0 or 1 |
| and | |
| n and p, | independently of one another, are 0, 1 or 2. |

The use of the compounds of the formulae IA and IB in the mixtures for SLCDs according to the invention produces high steepness of the electro-optical characteristic line low temperature dependence of the threshold voltage and very short response times, in particular at low temperatures.

The compounds of the formula IA are covered by the very broad generic claim in WO 95/30723 as components of liquid-crystalline media. However, the specific combination of the compounds of the formula IA with the compounds IB which produces, in particular, high steepness of the electro-optical characteristic line and low temperature dependence of the threshold voltage, is not described therein.

The compounds of the formulae IA and IB significantly shorten, in particular, the response times of SLCD mixtures while simultaneously increasing the steepness and retaining the low temperature dependence of the threshold voltage.

Furthermore, the mixtures according to the invention are distinguished by the following advantages:

they have low viscosity, they have low temperature dependence of the threshold voltage and the operating voltage, and they effect long storage times of the display at low temperatures.

The invention thus also includes to a liquid-crystal display having two outer plates which, together with a frame, form a cell, a nematic liquid-crystal mixture of positive dielectric anisotropy which is present in the cell, electrode layers with alignment layers on the insides of the outer plates, a pre-tilt angle between the longitudinal axis of the molecules at the surface of the outer plates and the outer plates of from about 0 degrees to 30 degrees, and a twist angle of the liquid-crystal mixture in the cell from alignment layer to alignment layer with a value of between 22.5° and 600°, a nematic liquid-crystal mixture consisting of
  a) 15–90% by weight of a liquid-crystalline component A consisting of one or more compounds having a dielectric anisotropy of greater than +1.5;
  b) 0–60% by weight of a liquid-crystalline component B consisting of one or more compounds having a dielectric anisotropy of between −1.5 and +1.5;
  c) 0–20% by weight of a liquid-crystalline component D consisting of one or more compounds having a dielectric anisotropy of below −1.5, and
  d) if desired, an optically active component C in such an amount that the ratio between the layer thickness (separation of the outer plates) and the natural pitch of the chiral nematic liquid-crystal mixture is from about 0.2 to 1.3, characterized in that the liquid-crystal mixture additionally comprises at least one compound of the formula IA

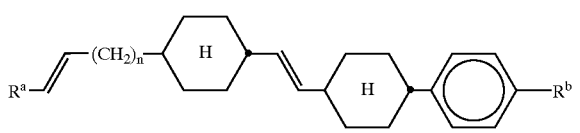

IA in which

| | |
|---|---|
| $R^a$ | is H or an alkyl group having 1 to 7 carbon atoms, |
| $R^b$ | is an alkyl or alkoxy group having 1 to 10 carbon atoms or an alkenyl or alkenyloxy group having 2 to 10 carbon atoms, |
| and | |
| n | is 0,1 or 2 | and simultaneously comprises at least one compound of the formula IB

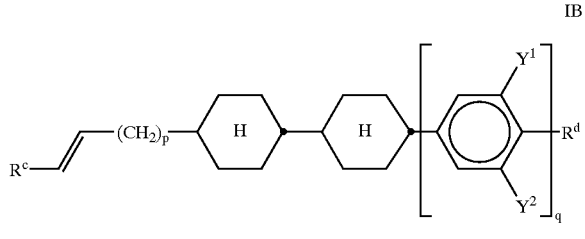

IB in which

| | |
|---|---|
| $R^c$ | is H or an alkyl group having 1 to 7 carbon atoms, |
| $R^d$ | is F, $OCF_3$, $OCHF_2$, an alkyl or alkoxy group having 1 to 7 carbon atoms or an alkenyl group having 2 to 7 carbon atoms, |
| $Y^1$ and $Y^2$, | independently of one another, are H or F, |
| p | is 0, 1 or 2, |
| q | is 0 or 1. |

The invention also relates to corresponding liquid-crystal mixtures for use in SLCDs, in particular in medium- and low-multiplexed SLCDs.

The compounds of the formulae IA and IB are prepared by methods known per se, as described in the literature (Houben-Weyl, Methoden der organischen Chemie [Methods of Organic Chemistry], Georg-Thieme-Verlag, Stuttgart), to be precise under reaction conditions which are known and suitable for said reactions.

Use can be made here of variants which are known per se, but are not mentioned here in greater detail.

The formula IB includes the following preferred compounds

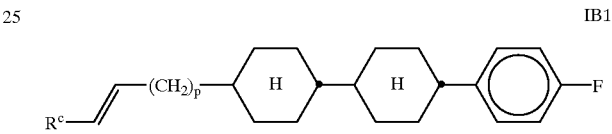

IB1

IB2

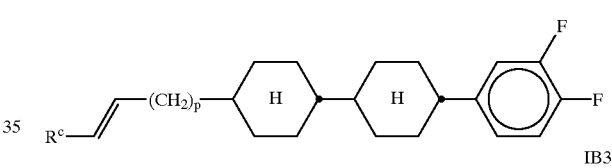

IB3

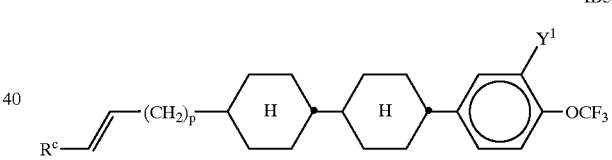

IB4

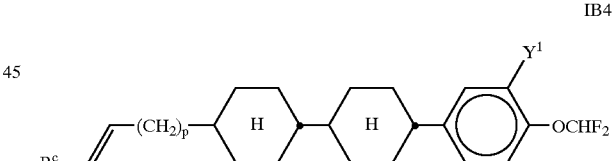

IB5

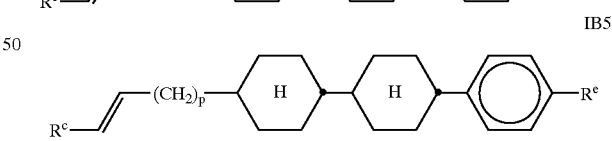

in which $R^c$, $Y^1$ and p are as defined above, and $R^e$ is an alkyl or alkoxy group having 1 to 7 carbon atoms. $R^e$ is particularly preferably methyl, ethyl, n-propyl, n-pentyl, methoxy, ethoxy, n-propoxy or n-butoxy.

Further preferred compounds of the formula IB are those of the sub-formulae IB6 and IB7

IB6

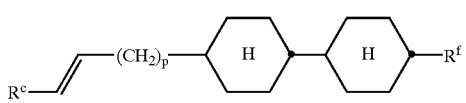
IB7 in which $R^c$ and $R^e$ are as defined above, and $R^f$ is alkenyl having 2 to 7 carbon atoms, in particular vinyl, 1E-propenyl, 1E-butenyl, 3E-butenyl, 1E-pentenyl or 3E-pentenyl.

Mixtures which, in addition to the compounds of the formula IA, comprise the compounds IB2, IB5, IB6 and/or IB7 are preferred.

Preferred compounds of the formulae IA and IB are those in which n and p, independently of one another, are 0 or 2.

$R^a$ and $R^c$ are preferably, independently of one another, H, a methyl group, an ethyl group or an n-propyl group, in particular H or a methyl group.

$R^b$ is preferably a straight-chain alkoxy group having 1 to 7 carbon atoms. In particular, $R^b$ is a methoxy, ethoxy or n-propoxy group. $R^b$ is very particularly preferably a methoxy group.

$R^d$ is preferably F, $OCF_3$, $OCHF_2$, a methyl, ethyl or n-propoxy group or a methoxy, ethoxy or n-propoxy group. $R^d$ is particularly preferably F, $OCF_3$ or $OCHF_2$.

Preference is given to compounds of the formulae IB in which $Y^1$ is F and $Y^2$ is simultaneously H. Preference is furthermore given to compounds of the formula IB in which $Y^1$ and $Y^2$ are simultaneously H.

Of the compounds of the formulae IA and IB and the sub-formulae, preference is given to those in which at least one of the radicals present therein has one of the preferred meanings indicated.

The compounds of the formula IB1, IB2 and IB7 are particularly preferred.

Component A preferably comprises compounds of the formulae II and/or III

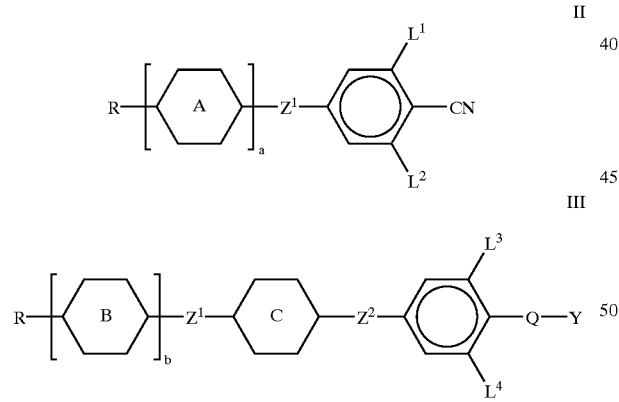

in which
R is an alkyl, alkoxy or alkenyl group having 1 to 12 carbon atoms, in which, in addition, one or two non-adjacent $CH_2$ groups may be replaced by —O—, —CH=CH—, —CO—, —OCO— or —COO— in such a way that O atoms are not linked directly to one another,

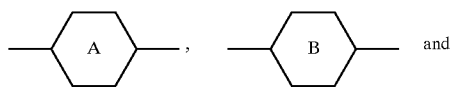
and

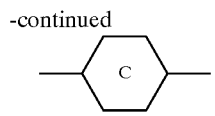

are each, independently of one another

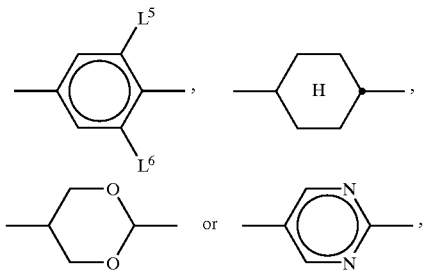

$L^1$ to $L^6$ are each, independently of one another, H or F,
$Z^1$ is —COO—, —$CH_2CH_2$— or a single bond,
$Z^2$ is —$CH_2CH_2$—, —COO—, —C≡C— or a single bond,
Q is —$CF_2$—, —CHF—, —$OCF_2$—, —OCHF— or a single bond,
Y is F or Cl
a is 1 or 2, and
b is 0 or 1, where compounds of the formula IB are excluded from the scope of the formula III.

Preferred compounds of the formula II conform to the sub-formulae IIa to IIh:

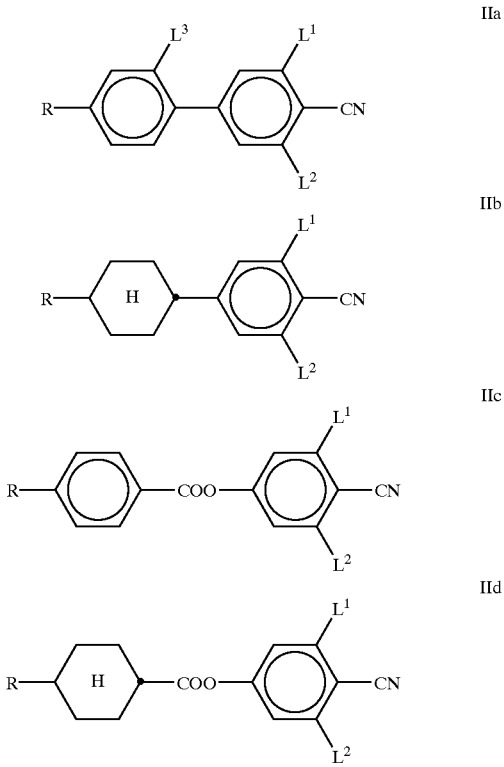

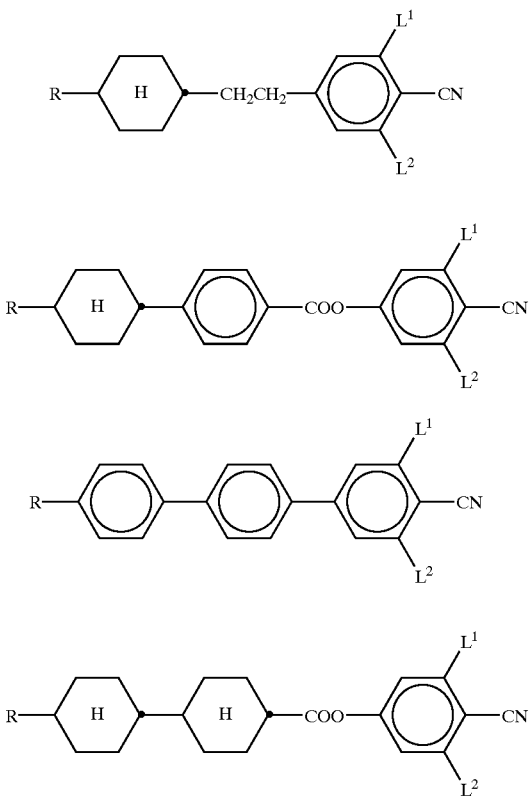

in which R, L$^1$, L$^2$ and L$^3$ are as defined above.

Particular preference is given to mixtures which comprise one or more compounds of the following sub-formulae

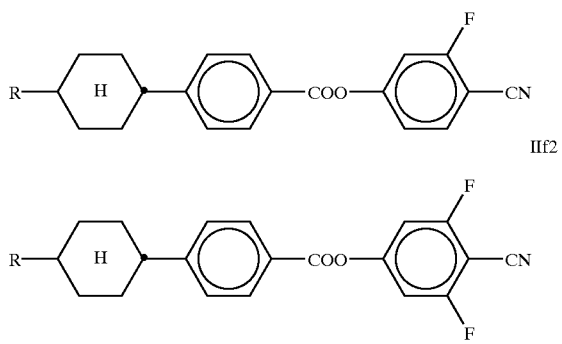

in which R is as defined above.

Preference is furthermore given to mixtures which comprise one or more compounds of the formula IIh in which L$^2$ is H and L$^1$ is H or F, in particular F.

In a particularly preferred embodiment, component A additionally comprises compounds of the formulae AI to AIV:

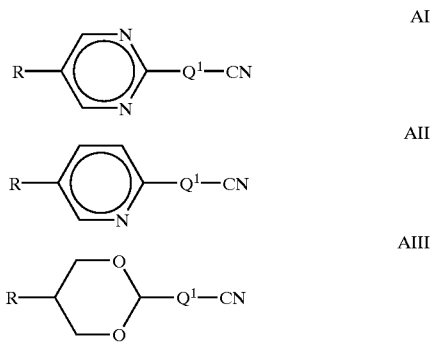

in which

R is an alkyl, alkoxy or alkenyl group having 1 to 12 carbon atoms, in which, in addition, one or two non-adjacent CH$_2$ groups may be replaced by —O—, —CH=CH—, —CO—, —OCO— or —COO— in such a way that O atoms are not linked directly to one another,

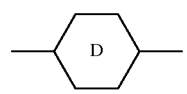

and Q$^1$ are each, independently of one another,

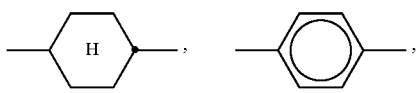

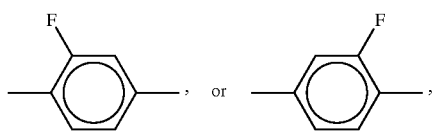

Z³ is

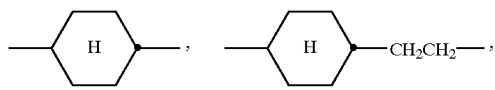

—CH₂CH₂—, —CO—O—, —O—CO— or a single bond.

The mixtures according to the invention preferably comprise one or more polar compounds having a high clearing point selected from the group consisting of the compounds AIV1 to AIV4:

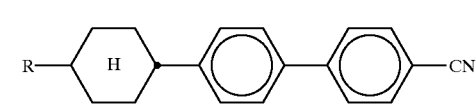

AIV1

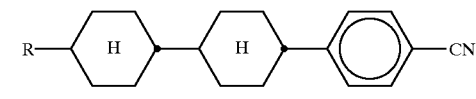

AIV2

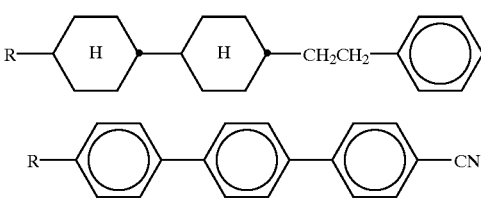

AIV3

AIV4

In the compounds AIV1 to AIV4, the 1,4-phenylene rings can also be laterally substituted by one or two fluorine atoms. Preferred compounds of this type are the compounds of the formulae AIV1-1, AIV1-2 and AIV1-3:

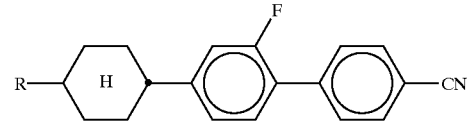

AIV1-1

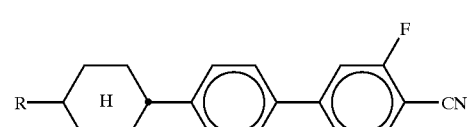

AIV1-2

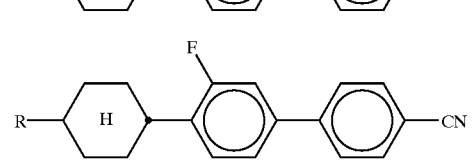

AIV1-3

In the mixtures according to the invention which comprise compounds of the formulae AIV1 to AIV4, the proportion of these compounds is preferably from about 2 to 25%.

Preferred compounds of the formula III conform to the sub-formulae IIIa–IIIv:

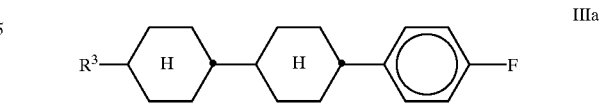

IIIa

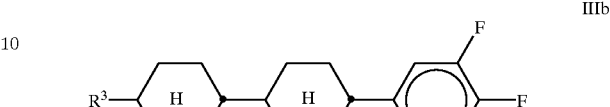

IIIb

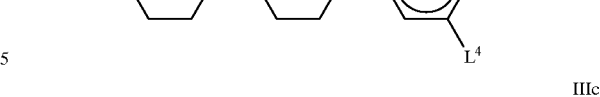

IIIc

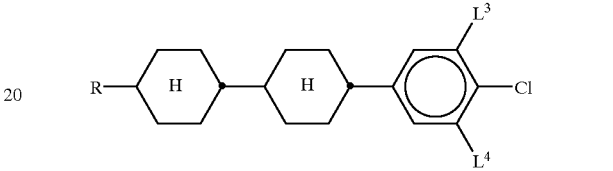

IIId

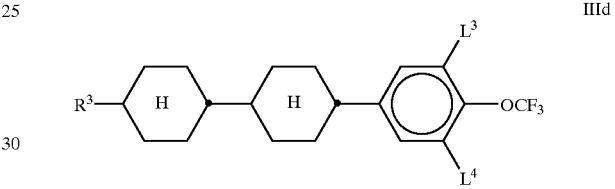

IIIe

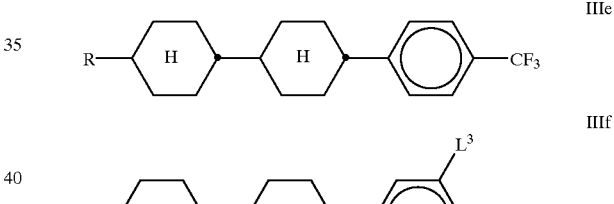

IIIf

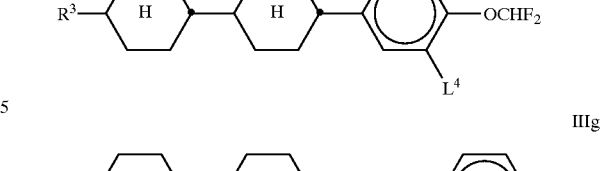

IIIg

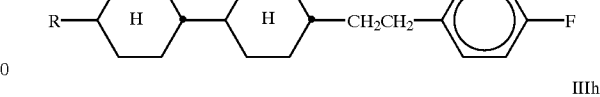

IIIh

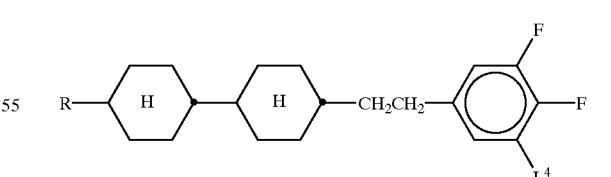

IIIi

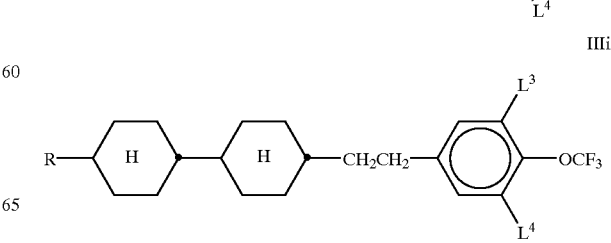

IIIj
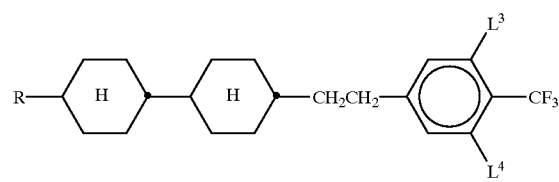

IIIk
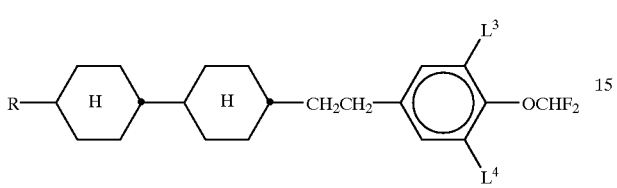

IIIm
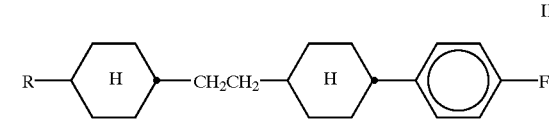

IIIn
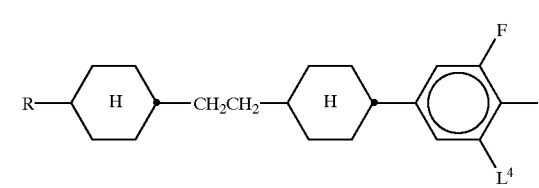

IIIo
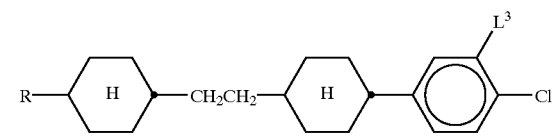

IIIp
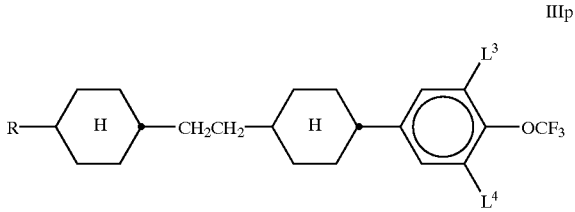

IIIq
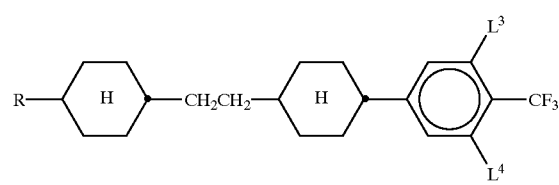

IIIr
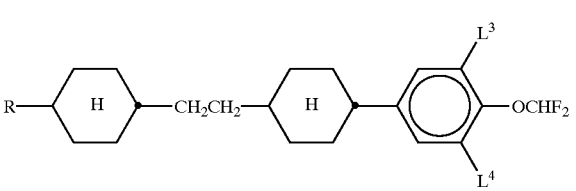

IIIs
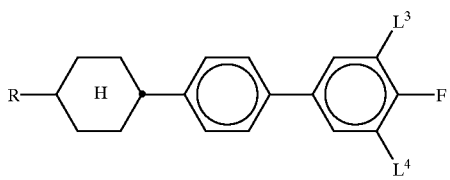

IIIt
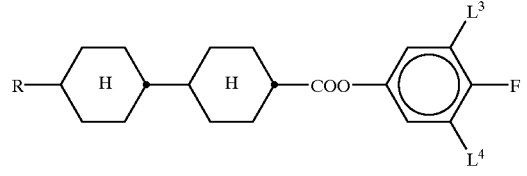

IIIu
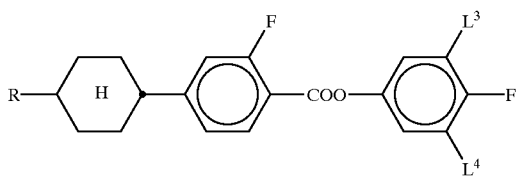

IIIv
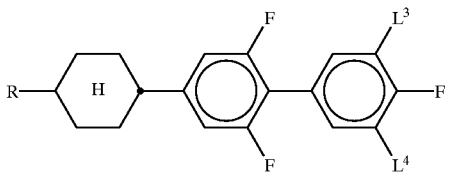

in which R is as defined above, $L^3$ and $L^4$, independently of one another, are H or F, and $R^3$ is alkyl or alkoxy having 1 to 7 carbon atoms.

Of the compounds of the formulae IIIa to IIIv, particular preference is given to those in which $L^4$ is F, furthermore those in which $L^3$ and $L^4$ are F.

In addition to one or more compounds of the formulae IA and IB, preferred mixtures comprise one, two, three or more compounds of the formulae IIa, IIb, IIc, IIf, IIIb, IIId, IIIf, IIIh, IIIi, IIIm, IIIs, IIIt or IIIu, preferably one or more compounds of the formula IIIb, IIId, IIIh, IIIt or IIIu, and from one to four compounds of the formulae IA and IB and from one to three compounds of the formulae IIa, IIb and/or IIc.

In the above- and below-mentioned preferred compounds of the sub-formulae to the formulae II and III, R, $R^1$ and $R^2$, unless stated otherwise, are preferably straight-chain alkyl, alkenyl or alkoxy, in particular alkyl, having 1 to 12 carbon atoms, in particular having 1 to 7 carbon atoms.

Preference is furthermore given to mixtures which comprise one or more compounds of the sub-formula IIIb1

IIIb1
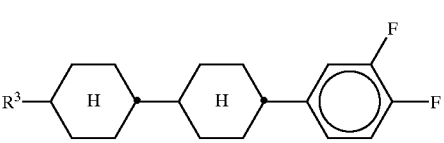

in which $R^3$ is as defined above.

In the compounds of the formula IIIb1, $R^3$ is particularly preferably n-propyl, n-pentyl or n-heptyl.

The individual compounds, for example of the formulae II and III or their sub-formulae, or alternatively other compounds which can be used in the SLCDs according to the invention, are either known or can be prepared analogously to known compounds.

Preferred liquid-crystal mixtures comprise none or small amounts of one or more compounds of Component B, preferably from 2 to 20%. The compounds of group B are distinguished, in particular, by their low rotational viscosity values $\gamma_1$.

Further preferred liquid-crystal mixtures comprise a plurality of compounds of Component A, preferably from 20 to 65%, particularly preferably from 30 to 50%.

Component B preferably comprises one or more compounds selected from the group consisting of the compounds of the formulae IV1 to IV9:

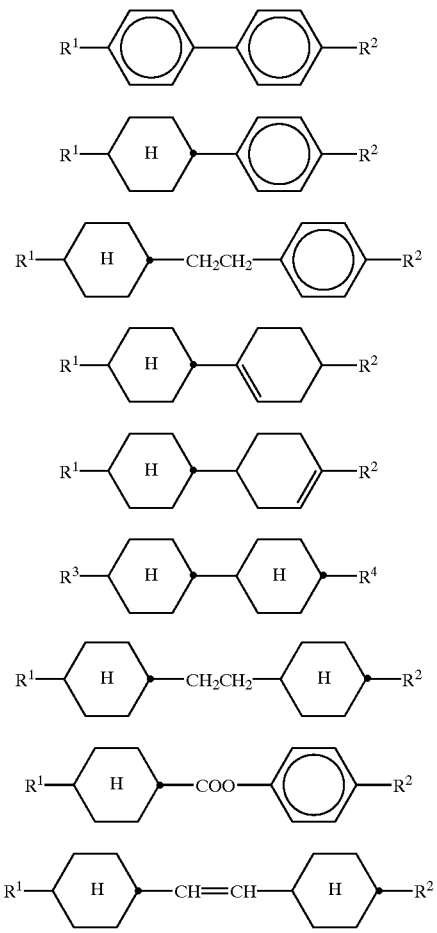

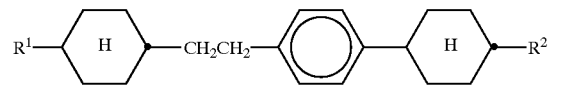
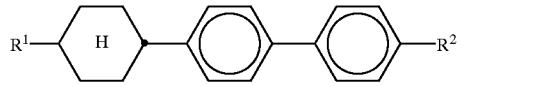
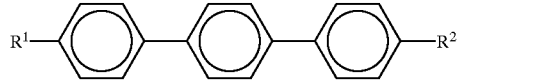
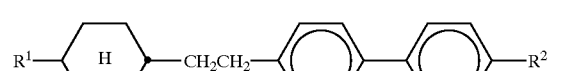
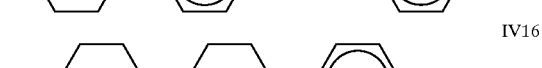
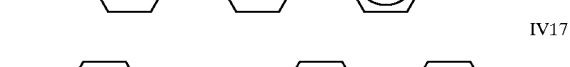
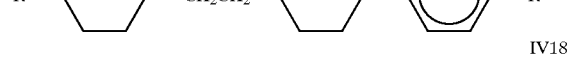
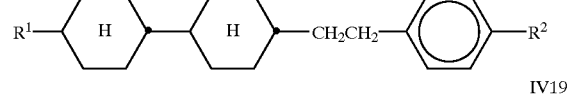
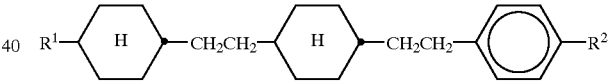
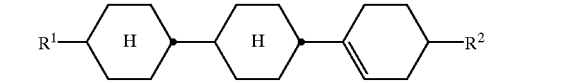
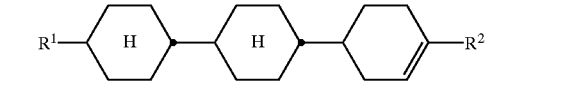
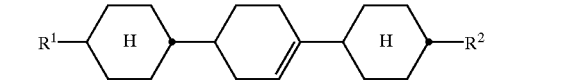
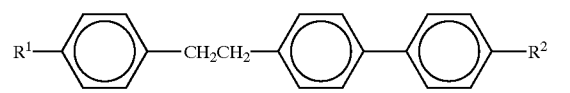

in which $R^1$ and $R^2$ are as defined for R, and $R^3$ and $R^4$, independently of one another, are an alkyl or alkoxy group having 1 to 7 carbon atoms.

Component B optionally additionally comprises one or more compounds selected from the group consisting of the compounds of the formulae IV10 to IV24:

in which $R^1$ and $R^2$ are as defined for R, $R^3$ and $R^4$, independently of one another, are an alkyl or alkoxy group having 1 to 7 carbon atoms, and the 1,4-phenylene groups in IV10 to IV19, IV23 and IV24 may each, independently of one another, also be monosubstituted or polysubstituted by fluorine.

Particular preference is given to mixtures comprising one or more compounds of the following formula:

IV12a

in which $R^{1\#}$ is alkenyl having 1 to 7 carbon atoms, and $R^{2\#}$ is straight-chain alkyl having 1 to 4 carbon atoms.

In these compounds, $R^{1\#}$ is particularly preferably vinyl, 1E-propenyl, 1-butenyl, 3E-butenyl or 3E-pentenyl. $R^{2\#}$ is particularly preferably methyl, ethyl or propyl, in particular methyl or ethyl.

Component B furthermore preferably comprises one or more compounds selected from the group consisting of the compounds of the formulae IV25 to IV31:

IV25

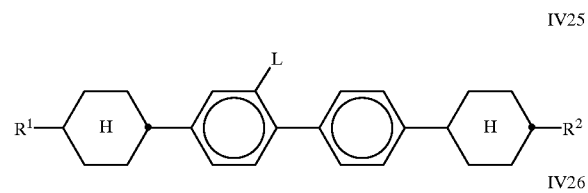

IV26

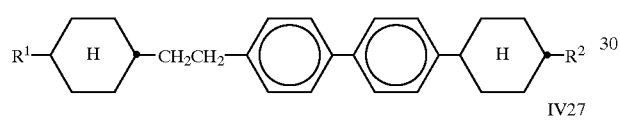

IV27

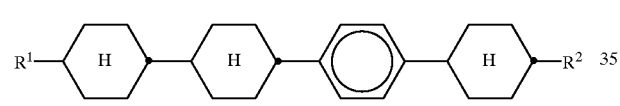

IV28

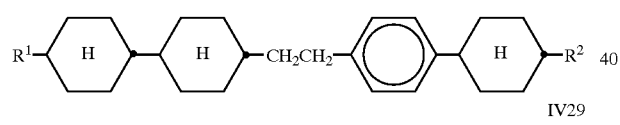

IV29

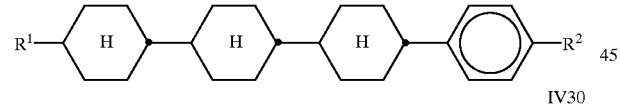

IV30

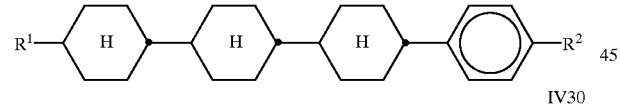

IV31

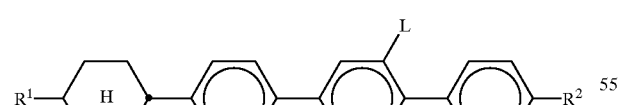

in which $R^1$ and $R^2$ are as defined for R, and L is F or H. The 1,4-phenylene groups in the compounds IV25 to IV31 may also each, independently of one another, be monosubstituted or polysubstituted by fluorine.

Mixtures which comprise compounds of the formula IV25 in which L is F are preferred.

Particular preference is given to compounds of the formulae IV25 to IV31 in which $R^1$ is alkyl and $R^2$ is alkyl or alkoxy, in particular alkoxy, in each case having 1 to 7 carbon atoms. Preference is furthermore given to compounds of the formulae IV25 and IV31 in which L is F.

In the compounds of the formulae IV1 to IV15 and IV17 to IV31, $R^1$ and $R^2$ are particularly preferably straight-chain alkyl or alkoxy having 1 to 12 carbon atoms.

Component B optionally comprises one or more compounds selected from the group consisting of the compounds of the formulae VI and VII:

VI

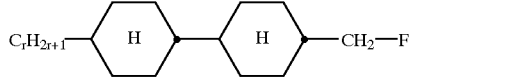

VII

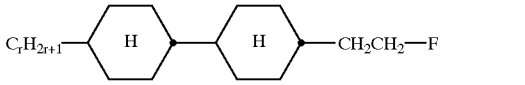

in which $C_rH_{2r+1}$ is a straight-chain alkyl group having up to 9 carbon atoms.

In a further preferred embodiment, the liquid-crystal mixtures according to the invention, besides components A, B, C and D, additionally comprise one or more compounds selected from the group consisting of the compounds of the formulae VIII and IX

VIII

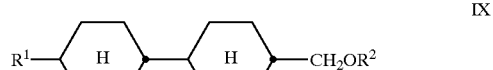

IX

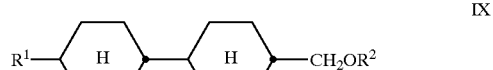

in which $R^1$ and $R^2$ are as defined above.

Preference is furthermore given to liquid-crystal mixtures comprising at least one component selected from the group consisting of the compounds of the formulae X to XIV:

X

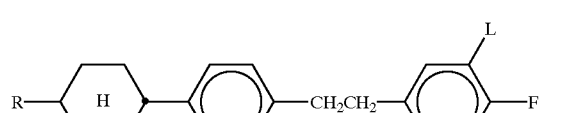

XI

XII

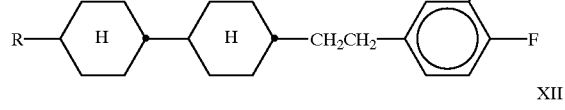

XIII

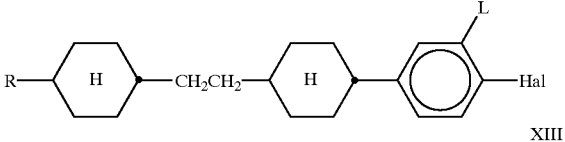

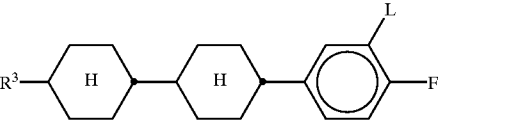

-continued

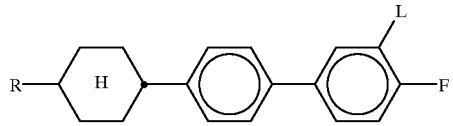
XIV in which Hal is F or Cl, L is H or F, and R and $R^3$ are as defined above, in particular in which R and $R^3$ are alkyl having 1 to 5 carbon atoms.

The liquid-crystalline mixtures optionally comprise an optically active component C in such an amount that the ratio between the layer thickness (separation of the outer plates) and the natural pitch of the chiral nematic liquid-crystal mixture is greater than 0.2. For the component, a multiplicity of chiral dopants, some of which are commercially available, is available to the person skilled in the art, for example such as cholesteryl nonanoate, S-811 from Merck KGaA, Darmstadt, and CB15 (BDH, Poole, UK). The choice of dopants is not crucial per se.

The proportion of the compounds of component C is preferably from 0 to 10%, in particular from 0 to 5%, particularly preferably from 0 to 3%

In a particularly preferred embodiment, the mixtures according to the invention comprise from about 2 to 45%, in particular from 5 to 25%, of liquid-crystalline tolan compounds. This enables smaller layer thicknesses to be used, significantly shortening the response times. The tolan compounds are preferably selected from Group T consisting of the compounds of the formulae T1, T2 and T3:

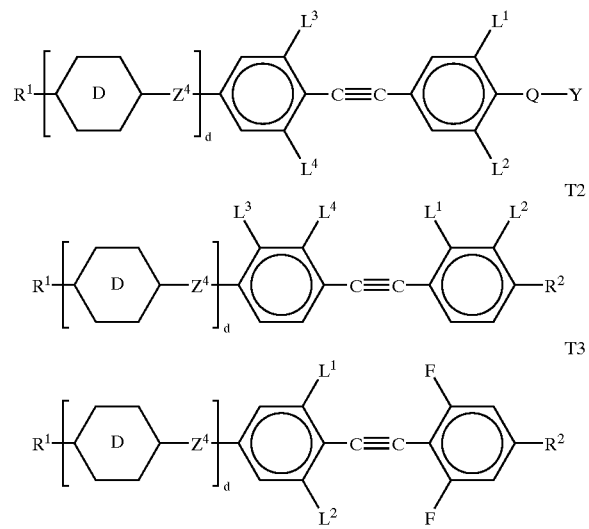

in which

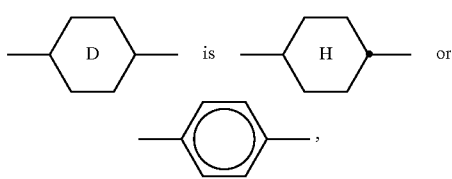

preferably

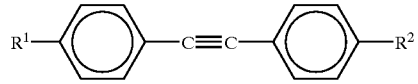

also

![](L5/L6 trisubstituted benzene)

in the formula T1 and also

![](L5/L6 disubstituted benzene)

in the formula T2,

| | |
|---|---|
| d | is 0 or 1, |
| $L^1$ to $L^6$ | are each, independently of one another, H or F, |
| Q | is —$CF_2$—, —CHF—, —$OCF_2$—, —OCHF— or a single bond, |
| Y | is F or Cl, |
| $Z^4$ | is —CO—O—, —$CH_2CH_2$— or a single bond, and |
| $R^1$ and $R^2$ | are as defined above. |

Preferred compounds of the formula T1 conform to the sub-formulae T1a and T1b

T1a

![T1a structure]

T1b

![T1b structure]

in which $L^1$ to $L^4$ are H or F, and Q—Y is F, Cl or $OCF_3$, in particular F or $OCF_3$.

Preferred compounds of the formula T2 conform to the sub-formulae T2a to T2g

T2a

![T2a structure]

-continued

T2b
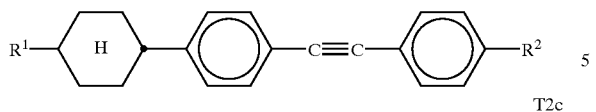

T2c
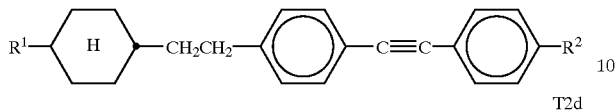

T2d
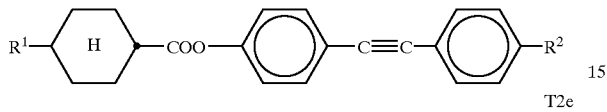

T2e
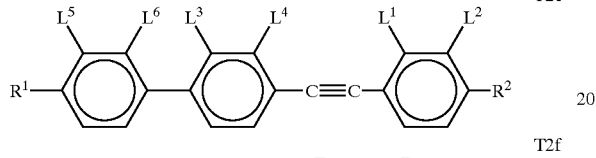

T2f
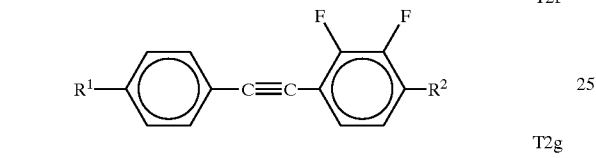

T2g
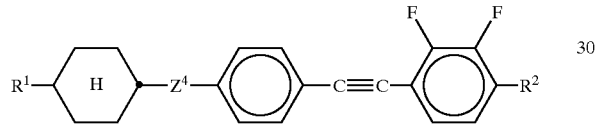

in which $R^1$, $R^2$ and $Z^4$ are as defined above, and $L^1$ to $L^6$ are H or F.

Particularly preferred compounds of the formula T2e are those in which one, two or three of the radicals $L^1$ to $L^6$ are F and the others are H, where $L^1$ and $L^2$ or $L^3$ and $L^4$ or $L^5$ and $L^6$ are not both simultaneously F.

Preferred compounds of the formula T3 conform to the sub-formulae T3a to T3e

T3a
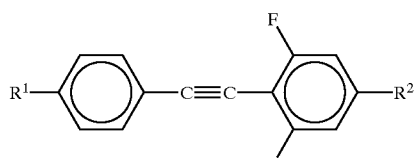

T3b
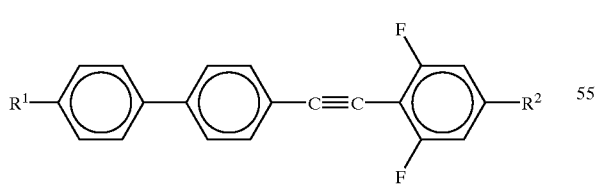

T3c
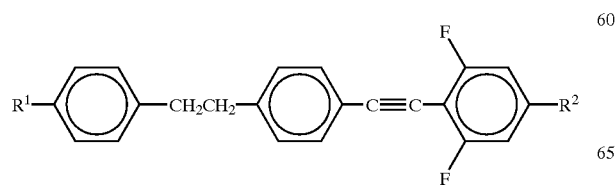

-continued

T3d
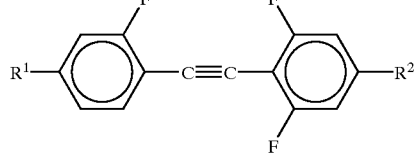

T3e
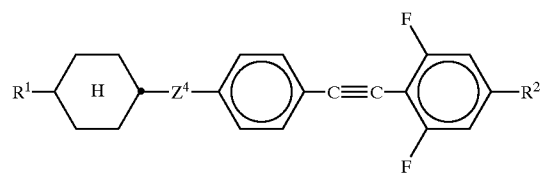

in which $R^1$, $R^2$ and $Z^4$ are as defined above.

The proportion of compounds from Group T is preferably from 2 to 45%, in particular from 5 to 30%.

In a further particularly preferred embodiment, the mixtures according to the invention preferably comprise from about 5 to 20% of one or more compounds having a dielectric anisotropy of less than −2 (component D).

Component) preferably comprises one or more compounds containing the structural unit 2,3-difluoro-1,4-phenylene, for example compounds as described in DE-A 38 07 801, 38 07 861, 38 07 863, 38 07 864 or 38 07 908. Particular preference is given to tolans containing this structural unit, as described in International Patent Application PCT/DE 88/00133, in particular those of the formulae T2f and T2g.

Further known compounds of component D are, for example, derivatives of 2,3-dicyanohydroquinones or cyclohexane derivatives containing the structural unit

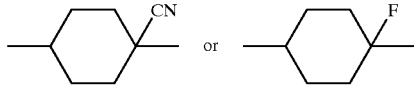

as described in DE-A 32 31 707 or DE-A 34 07 013 respectively.

The liquid-crystal mixture according to the invention preferably comprises one or more compounds selected from Group 1 consisting of compounds of the formulae B1I to B1IV:

B1I
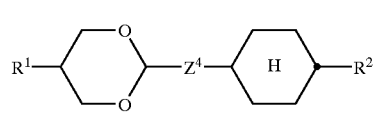

B1II
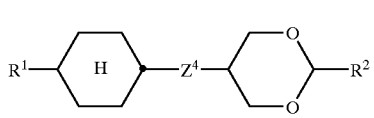

B1III
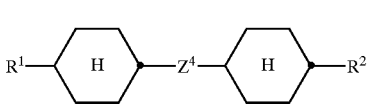

 B1IV in which $R^1$, $R^2$ and $Z^4$ are as defined above and

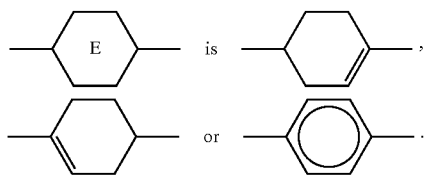

and/or at least one compound selected from Group B2 consisting of compounds of the formulae B2I to B2III:

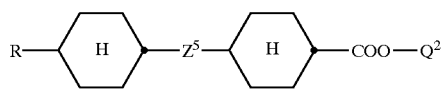 B2I

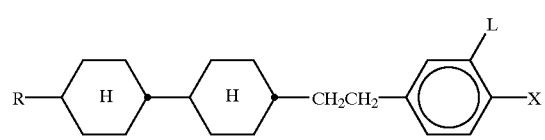 B2II

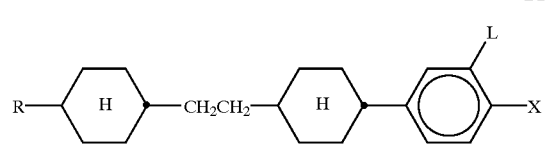 B2III in which

| | |
|---|---|
| R | is as defined above, |
| $Z^5$ | is —CH$_2$CH$_2$—, —CO—O— or a single bond, |
| $Q^2$ | is , |
| | 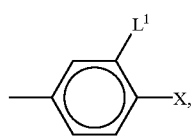 |
| alkyl | is an alkyl group having 1 to 9 carbon atoms, |
| X | is CN or F, and |
| L | is H or F, | and/or at least one compound selected from Group B3 consisting of compounds of the formulae B3I to B3III:

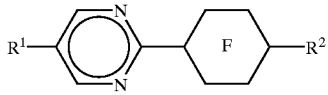 B3I

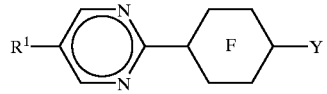 B3II

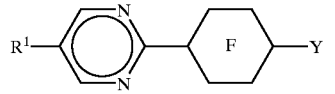 B3III in which

| | |
|---|---|
| $R^1$ and $R^2$, | independently of one another, are as defined above, |
| Y | is F or Cl, and |

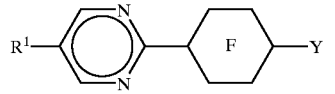

The proportion of the compounds from Group B1 is preferably from 10 to 50%, in particular from 15 to 40%. Compounds of the formulae B1III and B1IV are preferred.

Particularly preferred compounds from Group B1 are those of the following sub-formulae:

 B1IIIa

 B1IIIb

 B1IVa in which

| | |
|---|---|
| $R^{1a}$ | is CH$_3$—(CH$_2$)$_p$—, CH$_3$—(CH$_2$)$_p$—O—, CH$_3$—(CH$_2$)$_p$—O—CH$_2$—, trans-H—(CH$_2$)$_q$—CH=CH(CH$_2$CH$_2$)$_s$—CH$_2$O— or trans-H—(CH$_2$)$_q$—CH=CH—(CH$_2$CH$_2$)$_s$—, |
| $R^{2a}$ | is CH$_3$—(CH$_2$)$_p$—; |
| p | is 1, 2, 3 or 4, |
| s | is 0 or 1. |

The proportion of the compounds of the abovementioned sub-formulae B1IIIa and B1IIIb together with the compounds of the formula IB1 is preferably from about 5 to 45%, particularly preferably from about 10% to 35%.

The proportion of the compounds of the sub-formula B1IVa or of the compounds of the formula B1IV is preferably from about 5 to 40%, particularly preferably from about 10 to 35%.

In a particularly preferred embodiment, the mixtures simultaneously comprise compounds of the formulae B1III and B1IV together with the compounds of the formulae IB1 and IB2, where the total proportion for components from Group B1 is observed.

If compounds of the formulae B1I and/or B1III are present, $R^1$ and $R^2$ are preferably each, independently of one another, n-alkyl having 1 to 7 carbon atoms or (trans)-n-alkenyl having 3 to 7 carbon atoms. Z is preferably a single bond.

Preference is furthermore given to mixtures according to the invention which comprise one or more compounds of the formula B1IV in which

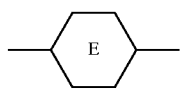

is

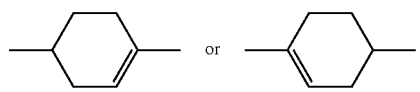

and $R^1$ and $R^2$ have one of the preferred meanings indicated above and are particularly preferably n-alkyl having 1 to 7 carbon atoms.

In all cases, the total proportion of components from Group B1 is observed.

The proportion of the compounds from group B2 is preferably from about 0 to 45%, in particular from 5 to 20%. The proportion (preferred ranges) for B2I to B2III is as follows:

| | |
|---|---|
| B2I: | from about 5 to 30%, preferably from about 5 to 15%, |
| sum of B2II and B2III: | from about 5 to 25%, preferably from about 10 to 20%. |

Preferred compounds from Group B2 are shown below:

B2Ia
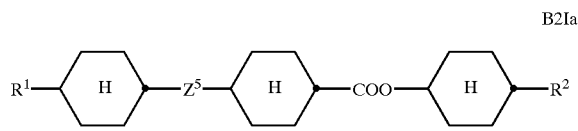

B2Ib
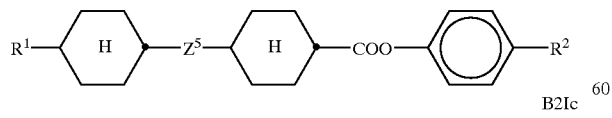

B2Ic
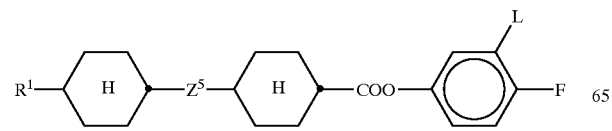

-continued

B2IIa
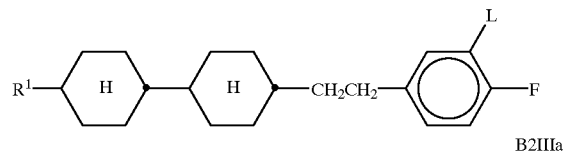

B2IIIa
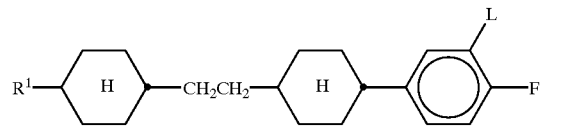

in which $R^1$, $R^2$, L and $Z^5$ are as defined above.

In these compounds, $R^1$ is preferably n-alkyl having 1 to 7 carbon atoms or (trans)-n-alkenyl having 3 to 7 carbon atoms, $Z^5$ is preferably a single bond, $R^2$ preferably has the preferred meaning given above for R or is fluorine, and L is preferably fluorine.

The mixtures according to the invention preferably comprise one or more compounds selected from the group consisting of B2Ic, B2IIa and B2IIIa in a total proportion of from about 5 to 35%

In a particularly preferred embodiment, the mixtures according to the invention, in addition to B2Ic, B2IIa and B2IIIa (L=F), comprise further terminally fluorinated compounds, selected, for example, from the group consisting of F1
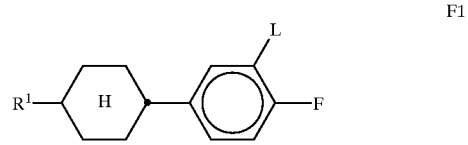

F2
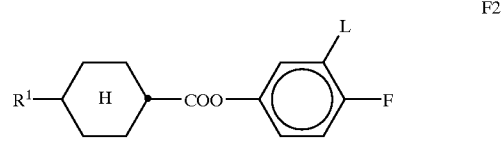

and/or polar heterocyclic compounds selected from the group consisting of

P1
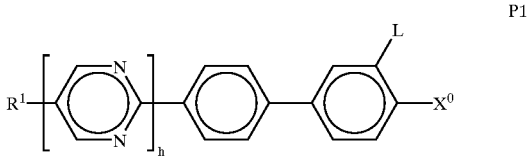

P2
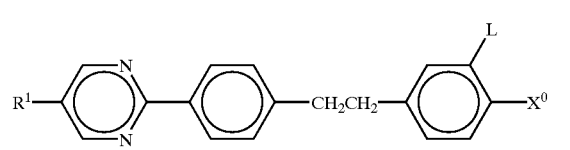

P3
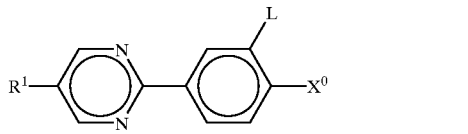

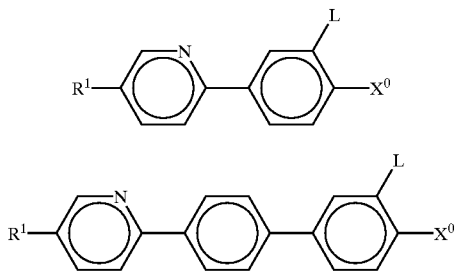

P4

P5 in which $R^1$ is preferably n-alkyl having 1 to 7 carbon atoms or (trans)-n-alkenyl having 3 to 7 carbon atoms, h is 0 or 1, $X^0$ is F, Cl, $CF_3$, —$OCF_3$ or —$OCHF_2$, and L is H or F.

The total proportion of all terminally fluorinated compounds is preferably from about 5 to 75%, in particular from about 15 to 50%.

The proportion of compounds from Group B3 is preferably from about 5 to 30%, particularly preferably from about 10 to 20%. $R^1$ is preferably n-alkyl or n-alkoxy, in each case having 1 to 9 carbon atoms.

However, it is also possible to employ analogous compounds containing alkenyl or alkenyloxy groups. Compounds of the formula B3I are preferred.

The term "alkenyl" in the definition of R, $R^1$, $R^2$, $R^f$ and $R^d$ covers straight-chain and branched alkenyl groups having carbon up to 7 atoms, in particular the straight-chain groups. Particularly preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl.

Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The terms "alkyl" and "alkoxy" in the definitions of $R^a$, $R^b$, $R^c$, $R^d$, $R^e$, R, $R^1$, $R^2$, $R^3$ and $R^4$ cover straight-chain and branched alkyl and alkoxy groups, in particular the straight-chain groups. Particularly preferred alkyl and alkoxy groups are ethyl, propyl, butyl, pentyl, hexyl, heptyl, ethoxy, propoxy, butoxy, pentoxy, hexyloxy or heptyloxy, furthermore methyl, octyl, nonyl, decyl, undecyl, dodecyl, methoxy, octyloxy, nonyloxy, decyloxy, undecyloxy or dodecyloxy.

The mixtures according to the invention comprise compounds of the formulae IA and IB and preferably compounds from at least one of groups B1, B2 and B3. They preferably comprise one or more compounds from Group B1 and one or more compounds from Group B2 and/or B3.

In a preferred embodiment, the liquid-crystalline media according to the invention comprise 3, 4, 5 or 6 compounds of the formulae IA and/or IB; the content of these compounds is generally from 10 to 80% by weight, preferably from 15 to 50% by weight, based on the mixture as a whole.

In a further preferred embodiment, the mixtures comprise one or more compounds of the following formulae

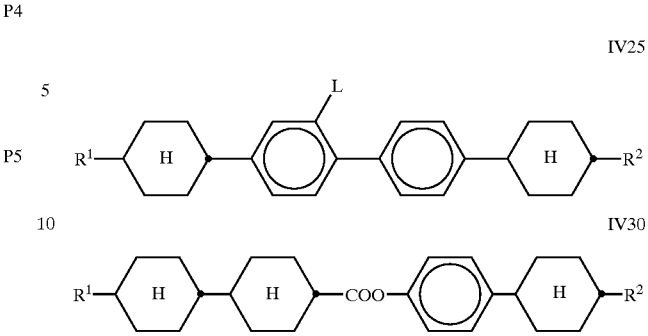

in which $R^1$, $R^2$ and L have the preferred meanings given under compounds of Component B. The proportion of these compounds in the liquid-crystal mixtures is preferably from 0 to 45%, in particular from 5 to 30%;

one or more, in particular 1, 2, 3 or 4, compounds selected from the compounds of the formulae IIIb, IIId, IIIf, IIIh, IIIi, IIIm, IIIs, IIIt and IIIu;

at least two compounds selected from the compounds of the formulae IIb1, IIb2, IIc1 and IIc2. The proportion of these compounds in the liquid-crystal mixtures is preferably from 0 to 60% by weight, particularly from 10 to 45%;

one or more compounds of the formula T1 or T2, in particular one or more compounds of the formula T2a and/or T2b, where the proportion of these compounds in the liquid-crystal mixtures is preferably from 0 to 25%, in particular from 1 to 15%.

Further particularly preferred embodiments relate to liquid-crystal mixtures comprising at least two compounds of the formula AI or AII;

one or more compounds in which R is a trans-alkenyl group or trans-alkenyloxy group;

one or more compounds selected from the following group:

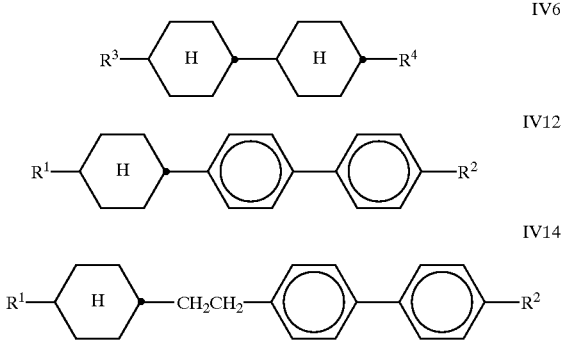

in which $R^1$, $R^2$ and L have the preferred meanings given under compounds of Component B, and $R^3$ and $R^4$ are as defined above. The 1,4-phenylene group in the abovementioned compounds may also be substituted by fluorine;

one or more compounds of the formulae

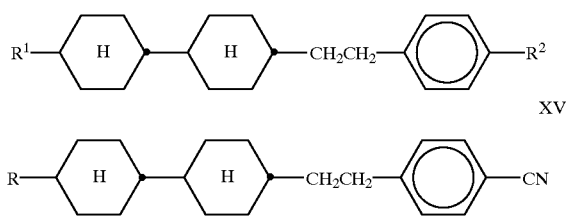

IV18

XV in which R, $R^1$ and $R^2$ are as defined above.

In particular when used in SLCDs having high layer thicknesses, the mixtures according to the invention are distinguished by very low total response times ($t_{tot}=t_{on}+t_{off}$). Low total response times are an important criterion, in particular, for SLCDs for use as displays in laptops in order to be able to display cursor movements without interference.

The liquid-crystal mixtures used in the STN and TN cells according to the invention are dielectrically positive with $\Delta \in \geq 1$. Particular preference is given to liquid-crystal mixtures where $\Delta \in \geq 3$ and very particularly to those where $\Delta \in \geq 5$.

The liquid-crystal mixtures according to the invention have favourable values for the threshold voltage $V_{10/0/20}$ and for the rotational viscosity $\gamma_1$. If the value for the optical path difference d·$\Delta$n is specified, the value for the layer thickness d is determined by the optical anisotropy $\Delta$n. In particular at relatively high values for d·$\Delta$n, the use of liquid-crystal mixtures according to the invention having a relatively high value for the optical anisotropy is generally preferred since the value for d can then be chosen to be relatively small, which results in more favourable values for the response times. However, liquid-crystal displays according to the invention which contain liquid-crystal mixtures according to the invention having relatively small values for $\Delta$n are also characterized by advantageous values for the response times.

The liquid-crystal mixtures according to the invention are furthermore characterized by advantageous values for the steepness of the electro-optical characteristic line and can be operated at high multiplex rates, in particular at temperatures above 20° C. In addition, the liquid-crystal mixtures according to the invention have high stability and favourable values for the electrical resistance and the frequency dependence of the threshold voltage. The liquid-crystal displays according to the invention have a broad operating temperature range and good angle dependence of the contrast.

The construction of the liquid-crystal display elements according to the invention from polarizers, electrode base plates and electrodes having a surface treatment such that the preferential alignment (director) of the liquid-crystal molecules in each case adjacent thereto is usually twisted by a value of from 160° to 720° from one electrode to the other corresponds to the structure which is conventional for display elements of this type. The term "conventional structure" is broadly drawn here and also includes all derivatives and modifications of the TN and STN cell, in particular also matrix display elements, and display elements which contain additional magnets.

The surface tilt angle at the two outer plates may be identical or different. Identical tilt angles are preferred. Preferred TN displays have pre-tilt angles between the longitudinal axis of the molecules at the surface of the outer plates and the outer plates of from 0° to 7°, preferably from 0.01° to 5°, in particular from 0.1 to 2°. In STN displays, the pre-tilt angle is from 1° to 30°, preferably from 1° to 12°, in particular from 3° to 10°.

The twist angle of the TN mixture in the cell has a value of between 22.5° and 170°, preferably between 45° and 130°, in particular between 80° and 115°. The twist angle of the STN mixture in the display from alignment layer to alignment layer has a value of between 100° and 600°, preferably between 170° and 300°, in particular between 180° and 270°.

The liquid-crystal mixtures which can be used according to the invention are prepared in a manner which is conventional per se. In general, the desired amount of the components used in a lesser amount is dissolved in the components making up the principal constituent, advantageously at elevated temperature. It is also possible to mix solutions of the components in an organic solvent, for example in acetone, chloroform or methanol, and, after mixing, to remove the solvent again, for example by distillation.

The dielectrics may also contain further additives which are known to the person skilled in the art and are described in the literature. For example, 0–15% of pleochroic dyes may be added.

The entire disclosure of all applications, patents and publications, cited above, and of corresponding German application No. 199 20 405.5, filed May 4, 1999 is hereby incorporated by reference.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

In the present application and in the examples below, the structures of the liquid-crystal compounds are indicated by acronyms, the transformation into chemical formulae taking place in accordance with Tables A and B below. All radicals $C_nH_{2n+1}$ and $C_mH_{2m+1}$ are straight-chain alkyl radicals having n and m carbon atoms respectively. The alkenyl radicals have the trans-configuration. The coding in Table B is self-evident. In Table A, only the acronym for the parent structure is given. In individual cases, the acronym for the parent structure is followed, separated by a hyphen, by a code for the substituents $R^1$, $R^2$, $L^1$, $L^2$ and $L^3$:

| Code for $R^1$, $R^2$, $L^1$, $L^2$, $L^3$ | $R^1$ | $R^2$ | $L^1$ | $L^2$ | $L^3$ |
|---|---|---|---|---|---|
| nm | $C_nH_{2n+1}$ | $C_mH_{2m+1}$ | H | H | H |
| nOm | $OC_nH_{2n+1}$ | $C_mH_{2m+1}$ | H | H | H |
| nO.m | $C_nH_{2n+1}$ | $OC_mH_{2m+1}$ | H | H | H |
| n | $C_nH_{2n+1}$ | CN | H | H | H |
| nN.F | $C_nH_{2n+1}$ | CN | H | H | F |

-continued

| Code for R$^1$, R$^2$, L$^1$, L$^2$, L$^3$ | R$^1$ | R$^2$ | L$^1$ | L$^2$ | L$^3$ |
|---|---|---|---|---|---|
| nN.F.F | C$_n$H$_{2n+1}$ | CN | H | F | F |
| nF | C$_n$H$_{2n+1}$ | F | H | H | H |
| nOF | OC$_n$H$_{2n+1}$ | F | H | H | H |
| nCl | C$_n$H$_{2n+1}$ | Cl | H | H | H |
| nF.F | C$_n$H$_{2n+1}$ | F | H | H | F |
| nmF | C$_n$H$_{2n+1}$ | C$_m$H$_{2m+1}$ | F | H | H |
| nCF$_3$ | C$_n$H$_{2n+1}$ | CF$_3$ | H | H | H |
| nOCF$_3$ | C$_n$H$_{2n+1}$ | OCF$_3$ | H | H | H |
| n-Am | C$_n$H$_{2n+1}$ | —C≡C—C$_m$H$_{2m+1}$ | H | H | H |
| n-AN | C$_n$H$_{2n+1}$ | —C≡C—CN | H | H | H |
| n-Vm | C$_n$H$_{2n+1}$ | —CH=CH—C$_m$H$_{2m+1}$ | H | H | H |
| nV-Vm | C$_n$H$_{2n+1}$—CH=CH— | —CH=CH—C$_m$H$_{2m+1}$ | H | H | H |

The TN and STN displays preferably contain liquid-crystalline mixtures composed of one or more compounds from Tables A and B.

TABLE A (L$^1$, L$^2$ and L$^3$ = H or F)

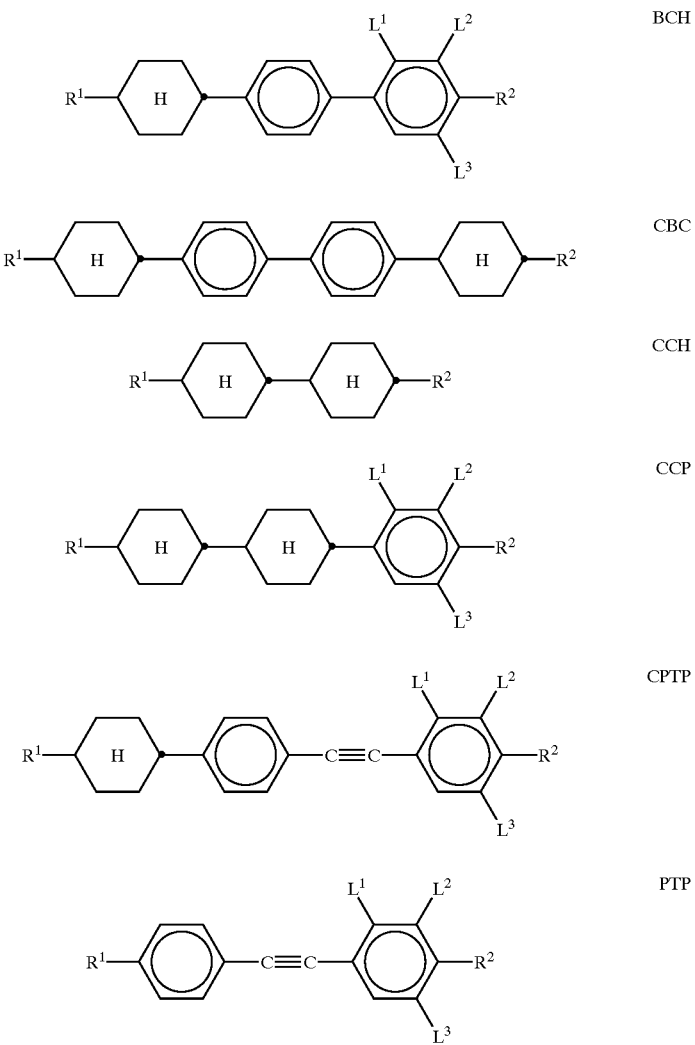

TABLE A-continued ($L^1$, $L^2$ and $L^3$ = H or F)

| Structure | Code |
|---|---|
| $R^1$—H—H—$C_2H_4$—(phenyl with $L^1$, $L^2$, $L^3$)—$R^2$ | ECCP |
| $R^1$—H—$C_2H_4$—(phenyl with $L^1$, $L^2$, $L^3$)—$R^2$ | EPCH |
| $R^1$—H—H—COO—(phenyl with $L^1$, $L^2$, $L^3$)—$R^2$ | CP |
| $R^1$—(phenyl)—COO—(phenyl with $L^1$, $L^2$, $L^3$)—$R^2$ | ME |
| $R^1$—H—(phenyl)—COO—(phenyl with $L^1$, $L^2$, $L^3$)—$R^2$ | HP |
| $R^1$—H—(phenyl with $L^1$, $L^2$, $L^3$)—$R^2$ | PCH |
| $R^1$—H—H—COO—(phenyl)—(phenyl)—H—$R^2$ | CCPC |

TABLE B

| Structure | Code |
|---|---|
| $C_nH_{2n+1}$—H—$C_2H_4$—(phenyl)—(phenyl with F)—$C_mH_{2m+1}$ | Inm |
| $C_nH_{2n+1}$—(phenyl)—(phenyl)—CN | K3n |

TABLE B-continued

| Structure | Code |
|---|---|
| $C_nH_{2n+1}$–CH=CH–[H]–[H]–⌬–$C_mH_{2m+1}$ | CCP-nV-m |
| CH$_2$=CH–[H]–[H]–⌬(3,4-F$_2$) | CCG-V-F |
| $C_nH_{2n+1}$–[H]–⌬(2-F)–⌬–[H]–$C_mH_{2m+1}$ | CBC-nmF |
| $C_nH_{2n+1}$–[H]–[H]–CH=CH$_2$ | CC-n-V |
| $C_nH_{2n+1}$–[H]–⌬(2,6-F$_2$)–C≡C–CN | CU-n-AN |
| $C_nH_{2n+1}$–CH=CH–[H]–[H]–CH=CH–$C_mH_{2m+1}$ | CC-nV-Vm |
| H$_2$C=CH–[H]–[H]–⌬–$C_mH_{2m+1}$ | CCP-V-m |
| $C_nH_{2n+1}$–CH$_2$CH$_2$CH=CH–[H]–[H]–⌬–$C_mH_{2m+1}$ (H$_2$C=CH-CH$_2$-CH$_2$-) | CCP-V2-m |
| $C_nH_{2n+1}$–⌬–⌬–C≡C–⌬(2,6-F$_2$)–$C_mH_{2m+1}$ | PPTUI-n-m |
| $C_nH_{2n+1}$–CH=CH–CH$_2$CH$_2$–[H]–⌬–⌬–$C_mH_{2m+1}$ | CCP-nV2-m |
| $C_nH_{2n+1}$–CH=CH–[H]–CH=CH–[H]–⌬–$C_mH_{2m+1}$ | CVCP-nV-m |

TABLE B-continued

CVCP-nV-Om: $C_nH_{2n+1}$—CH=CH—[H]—CH=CH—[H]—[phenyl]—$OC_mH_{2m+1}$

CVCP-nV2-m: $C_nH_{2n+1}$—CH$_2$—CH=CH—[H]—CH=CH—[H]—[phenyl]—$C_mH_{2m+1}$

CVCP-nV2-Om: $C_nH_{2n+1}$—CH$_2$—CH=CH—[H]—CH=CH—[H]—[phenyl]—$OC_mH_{2m+1}$

The examples below are intended to illustrate the invention without representing a limitation.

| | |
|---|---|
| S-N | smectic-nematic phase transition temperature |
| N-I | nematic-isotropic phase transition temperature |
| cl.p. | clearing point |
| visc. | rotational viscosity (mPa · s) |
| $\Delta n$ | optical anisotropy (589 nm, 20° C.) |
| $\Delta\epsilon$ | dielectric anisotropy (1 kHz, 20° C.) |
| $t_{on}$ | time from switching on until 90% of the maximum contrast is achieved |
| $t_{off}$ | time from switching off until 10% of the maximum contrast is achieved |
| $V_{10}$ | threshold voltage = characteristic voltage at a relative contrast of 10% (also abbreviated to $V_{(10,0,20)}$) |
| $V_{90}$ | characteristic voltage at a relative contrast of 90% |
| $V_{90}/V_{10}$ | steepness |
| $V_{op}$ | operating voltage |
| $t_{ave}$ | $(t_{on} + t_{off})/2$ (average response time) |
| d | cell thickness |
| p | pitch |

Above and below, all temperatures are given in °C. Percentages are per cent by weight. The values for the response times and viscosities relate to 20° C., unless states otherwise. The response time is, unless stated otherwise, the average value $t_{ave}$ of the switch-on and switch-off times.

The SLCD is, unless stated otherwise, addressed with a rectangular voltage of 80 Hz.

Example 1

An STN mixture comprising

| | | | |
|---|---|---|---|
| ME2N.F | 5.00% | Clearing point: | 77.0° C. |
| ME3N.F | 5.00% | $\Delta n$: | 0.1423 |
| ME4N.F | 6.00% | Twist: | 240° |
| PCH-3N.F.F | 18.00% | $V_{10}$: | 1.37 V |
| PCH-3 | 9.00% | $V_{90}/V_{10}$: | 1.044 |
| CC-1V-V1 | 8.00% | d · $\Delta n$: | 0.85 µm |
| CCG-V-F | 10.00% | | |
| CCP-V-1 | 13.50% | | |
| CVCP-V-O1 | 5.00% | | |
| CVCP-1V-O1 | 5.00% | | |
| PTP-102 | 5.50% | | |
| PTP-201 | 2.00% | | |
| CPTP-301 | 5.50% | | |
| CPTP-302 | 2.50% | | |

Example 2

An STN mixture comprising

| | | | |
|---|---|---|---|
| ME2N.F | 5.00% | Clearing point: | 76.5° C. |
| ME3N.F | 5.00% | $\Delta n$: | 0.1410 |
| ME4N.F | 6.00% | Twist: | 240° |
| PCH-3N.F.F | 18.00% | $V_{10}$: | 1.35 V |
| PCH-3 | 9.00% | $V_{90}/V_{10}$: | 1.045 |
| CC-3-V1 | 8.00% | d · $\Delta n$: | 0.85 µm |
| CCG-V-F | 9.00% | | |
| CCP-V-1 | 14.00% | | |
| CVCP-V-O1 | 5.00% | | |
| CVCP-1V-O1 | 5.00% | | |
| PTP-102 | 5.50% | | |
| PTP-201 | 2.00% | | |
| CPTP-301 | 5.50% | | |
| CPTP-302 | 3.00% | | |

Example 3

An STN mixture comprising

| | | | |
|---|---|---|---|
| ME2N.F | 5.00% | Clearing point: | 76.0° C. |
| ME3N.F | 5.00% | $\Delta n$: | 0.1410 |
| ME4N.F | 6.00% | Twist: | 240° |
| PCH-3N.F.F | 18.00% | $V_{10}$: | 1.36 V |
| PCH-3 | 9.00% | $V_{90}/V_{10}$: | 1.064 |
| CC-3-V1 | 8.00% | d · $\Delta n$: | 0.85 µm |
| CCG-V-F | 6.00% | | |
| CCP-V-1 | 17.00% | | |
| CVCP-V-1 | 5.00% | | |
| CVCP-1V-1 | 5.00% | | |
| PTP-102 | 5.50% | | |
| PTP-201 | 1.50% | | |
| CPTP-301 | 6.00% | | |
| CPTP-302 | 3.00% | | |

Example 4

An STN mixture comprising

| | | | |
|---|---|---|---|
| PCH-3N.F.F | 10.00% | Clearing point: | 96.0° C. |
| ME2N.F | 6.00% | $\Delta n$: | 0.1399 |
| ME3N.F | 6.00% | Twist: | 240° |
| ME4N.F | 9.00% | $V_{10}$: | 1.29 V |
| ME5N.F | 9.00% | $V_{90}/V_{10}$: | 1.043 |
| CC-5-V | 3.00% | $d \cdot \Delta n$: | 0.85 µm |
| CCG-V-F | 15.00% | | |
| CCP-V-1 | 9.00% | | |
| CVCP-V-1 | 5.00% | | |
| CVCP-1V-1 | 5.00% | | |
| CVCP-V-O1 | 5.00% | | |
| CVCP-1V-O1 | 5.00% | | |
| PTP-102 | 3.00% | | |
| CPTP-301 | 3.00% | | |
| CBC-33F | 4.00% | | |
| CBC-53F | 3.00% | | |

Example 5

An STN mixture comprising

| | | | |
|---|---|---|---|
| PCH-3N.F.F | 10.00% | Clearing point: | 95.0° C. |
| ME2N.F | 6.00% | $\Delta n$: | 0.1386 |
| ME3N.F | 6.00% | Twist: | 240° |
| ME4N.F | 9.00% | $V_{10}$: | 1.27 V |
| ME5N.F | 9.00% | $V_{90}/V_{10}$: | 1.039 |
| CC-5-V | 3.00% | $d \cdot \Delta n$: | 0.85 µm |
| CCG-V-F | 15.00% | | |
| CCP-V-1 | 9.00% | | |
| CCP-V2-1 | 5.00% | | |
| CVCP-V-1 | 5.00% | | |
| CVCP-V-O1 | 5.00% | | |
| CVCP-1V-O1 | 5.00% | | |
| PTP-102 | 3.00% | | |
| CPTP-301 | 3.00% | | |
| CBC-33F | 4.00% | | |
| CBC-53F | 3.00% | | |

Example 6

An STN mixture comprising

| | | | |
|---|---|---|---|
| PCH-3N.F.F | 10.00% | Clearing point: | 95.0° C. |
| ME2N.F | 6.00% | $\Delta n$: | 0.1380 |
| ME3N.F | 6.00% | Twist: | 240° |
| ME4N.F | 9.00% | $V_{10}$: | 1.27 V |
| ME5N.F | 9.00% | $V_{90}/V_{10}$: | 1.053 |
| CC-5-V | 3.00% | $d \cdot \Delta n$: | 0.85 µm |
| CCG-V-F | 15.00% | | |
| CCP-V-1 | 9.00% | | |
| CCP-V2-1 | 10.00% | | |
| CVCP-V-O1 | 5.00% | | |
| CVCP-1V-O1 | 5.00% | | |
| PTP-102 | 3.00% | | |
| CPTP-301 | 3.00% | | |
| CBC-33F | 4.00% | | |
| CBC-53F | 3.00% | | |

Example 7

An STN mixture comprising

| | | | |
|---|---|---|---|
| ME2N.F | 4.00% | Clearing point: | 97.0° C. |
| ME3N.F | 4.00% | $\Delta n$: | 0.1734 |
| ME4N.F | 10.00% | Twist: | 240° |
| PCH-3N.F.F | 18.00% | $V_{10}$: | 1.44 V |
| CC-5-V | 11.50% | $V_{90}/V_{10}$: | 1.074 |
| CVCP-V-O1 | 4.00% | | |
| CVCP-1V-O1 | 4.00% | | |
| CCP-V-1 | 14.00% | | |
| CBC-33F | 5.00% | | |
| CBC-53F | 3.00% | | |
| PPTUI-3-2 | 22.50% | | |

Example 8

An STN mixture comprising

| | | | |
|---|---|---|---|
| PCH-3N.F.F | 19.00% | Clearing point: | 91.0° C. |
| ME2N.F | 4.00% | $\Delta n$: | 0.1423 |
| ME3N.F | 4.00% | Twist: | 240° |
| ME4N.F | 10.00% | $V_{10}$: | 1.43 V |
| CC-5-V | 3.00% | $V_{90}/V_{10}$: | 1.054 |
| CC-3-V1 | 7.00% | $d \cdot \Delta n$: | 0.85 µm |
| CVCP-V-O1 | 4.00% | | |
| CVCP-V-1 | 4.50% | | |
| CCP-V-1 | 15.00% | | |
| CCP-V2-1 | 14.00% | | |
| PPTUI-3-2 | 11.50% | | |
| CVCP-1V-O1 | 4.00% | | |

Example 9

An STN mixture comprising

| | | | |
|---|---|---|---|
| ME2N.F | 2.00% | Clearing point: | 85.0° C. |
| ME3N.F | 3.00% | $\Delta n$: | 0.1411 |
| ME4N.F | 6.00% | Twist: | 240° |
| PCH-3N.F.F | 17.00% | $V_{10}$: | 1.48 V |
| PCH-3 | 19.00% | $V_{90}/V_{10}$: | 1.043 |
| CVCP-V-O1 | 4.00% | $d \cdot \Delta n$: | 0.85 µm |
| CVCP-1V-O1 | 4.00% | | |
| CCP-V-1 | 15.00% | | |
| CCP-V2-1 | 14.00% | | |
| CCG-V-F | 6.00% | | |
| PPTUI-3-2 | 10.00% | | |

Example 10

An STN mixture comprising

| | |
|---|---|
| ME2N.F | 2.00% |
| ME3N.F | 2.00% |
| PCH-3N.F.F | 13.00% |
| PCH-3 | 26.00% |
| CVCF-V-O1 | 4.00% |
| CVCP-1V-O1 | 4.00% |
| CC-3-V1 | 6.00% |
| CCP-V-1 | 14.00% |
| CCP-V2-1 | 13.00% |
| CCG-V-F | 5.00% |
| PPTUI-3-2 | 11.00% |
| Clearing point: | 92.0° C. |

|  |  |
|---|---|
| Δn: | 0.1411 |
| Twist: | 240° |
| $V_{10}$: | 1.81 V |
| $V_{90}/V_{10}$: | 1.039 |
| d · Δn: | 0.85 μm |

Example 11

An STN mixture comprising

|  |  |
|---|---|
| ME2N.F | 6.00% |
| ME3N.F | 6.00% |
| ME4N.F | 10.00% |
| ME5N.F | 10.00% |
| FCH-3N.F.F | 10.00% |
| CCG-V-F | 10.00% |
| CC-5-V | 10.00% |
| CCP-V-1 | 9.00% |
| CVCP-V-O1 | 5.00% |
| CVCP-1V-O1 | 5.00% |
| CCPC-33 | 4.00% |
| CCPC-34 | 3.00% |
| CPTP-301 | 4.00% |
| CPTP-302 | 4.00% |
| CPTP-303 | 4.00% |
| Clearing point: | 98.0° C. |
| Δn: | 0.1414 |
| Twist: | 240° |
| $V_{10}$: | 1.28 V |
| $V_{90}/V_{10}$: | 1.062 |
| d · Δn: | 0.85 μm |

Example 12

An STN mixture comprising

|  |  |
|---|---|
| ME2N.F | 7.00% |
| ME3N.F | 7.00% |
| ME4N.F | 10.00% |
| ME5N.F | 10.00% |
| CP-1V-N | 12.00% |
| CP-V2-N | 19.00% |
| CCP-V-1 | 10.00% |
| CVCP-V-O1 | 5.00% |
| CVCP-1V-O1 | 5.00% |
| CCPC-33 | 5.00% |
| CCPC-34 | 5.00% |
| CCPC-35 | 5.00% |
| Clearing point: | +94.5° C. |
| Δn: | 0.1447 |
| Twist: | 240° |
| $V_{10}$: | 1.33 V |
| $V_{90}/V_{10}$: | 1.023 |
| d · Δn: | 0.85 μm |

Example 13

An STN mixture comprising

|  |  |
|---|---|
| ME2N.F | 6.00% |
| ME3N.F | 6.00% |
| ME4N.F | 9.00% |
| ME5N.F | 9.00% |
| CP-1V-N | 11.00% |
| CP-V2-N | 11.00% |
| CC-5-V | 10.00% |
| CCP-V-1 | 15.00% |
| CVCP-V-O1 | 5.00% |
| CVCP-1V-O1 | 5.00% |
| CCPC-33 | 4.00% |
| CCPC-34 | 3.00% |
| CPTP-301 | 3.00% |
| CPTP-302 | 3.00% |
| Clearing point: | +96.5° C. |
| Δn: | +0.1424 |
| Twist: | 240° |
| $V_{10}$: | 1.47 V |
| $V_{90}/V_{10}$: | 1.029 |
| d · Δn: | 0.85 μm |

Example 14

An STN mixture comprising

|  |  |
|---|---|
| PCH-3 | 20.00% |
| PCH-3N.F.F | 20.00% |
| CC-5-V | 1.00% |
| CCG-V-F | 17.00% |
| CCP-V-1 | 15.00% |
| CVCP-V-1 | 5.00% |
| CVCP-V-O1 | 5.00% |
| CVCP-1V-O1 | 4.00% |
| PTP-102 | 3.00% |
| CPTP-301 | 5.00% |
| CPTP-302 | 5.00% |
| Clearing point: | +92.0° C. |
| Δn: | +0.1321 |
| Twist: | 240° |
| $V_{10}$: | 1.78 V |
| $V_{90}/V_{10}$: | 1.029 |
| d · Δn: | 0.85 μm |

Example 15

An STN mixture comprising

|  |  |
|---|---|
| PCH-3 | 20.00% |
| PCH-3N.F.F | 18.00% |
| ME2N.F | 1.00% |
| ME3N.F | 1.00% |
| CCG-V-F | 16.00% |
| CCP-V-1 | 15.00% |
| CCP-V2-1 | 2.50% |
| CVCP-V-1 | 5.00% |
| CVCP-V-O1 | 5.00% |
| CVCP-1V-O1 | 5.00% |
| PTP-102 | 5.00% |
| CPTP-302 | 5.00% |
| CPTP-303 | 1.50% |
| Clearing point: | +91.5° C. |
| Δn: | +0.1329 |
| Twist: | 240° |
| $V_{10}$: | 1.77 V |
| $V_{90}/V_{10}$: | 1.027 |
| d · Δn: | 0.85 μm |

Example 16

An STN mixture comprising

| | |
|---|---|
| PCH-3N.F.F | 11.00% |
| ME2N.F | 6.00% |
| ME3N.F | 6.00% |
| ME4N.F | 9.00% |
| ME5N.F | 9.00% |
| CC-5-V | 3.00% |
| CCG-V-F | 13.00% |
| CCP-V-1 | 16.00% |
| CVCP-V-1 | 5.00% |
| CVCP-V-O1 | 5.00% |
| CVCP-1V-O1 | 5.00% |
| CBC-33F | 3.00% |
| CBC-53F | 3.00% |
| CBC-55F | 3.00% |
| CCPC-33 | 3.00% |
| Clearing point: | +101.0° C. |
| $\Delta n$: | +0.1291 |
| Twist: | 240° |
| $V_{10}$: | 1.29 V |
| $V_{90}/V_{10}$: | 1.052 |
| $d \cdot \Delta n$: | 0.85 µm |

Example 17

An STN mixture comprising

| | |
|---|---|
| PCH-3N.F.F | 14.00% |
| ME2N.F | 4.00% |
| ME3N.F | 4.00% |
| ME4N.F | 6.00% |
| ME5N.F | 6.00% |
| CC-5-V | 4.00% |
| CCG-V-F | 18.50% |
| CCP-V-1 | 16.00% |
| CVCP-V-1 | 5.00% |
| CVCP-V-O1 | 5.00% |
| CVCP-1V-O1 | 5.00% |
| PTP-102 | 2.00% |
| CPTP-302 | 3.50% |
| CBC-33F | 3.00% |
| CBC-53F | 2.00% |
| CBC-55F | 2.00% |
| Clearing point: | +101.0° C. |
| $\Delta n$: | +0.1298 |
| Twist: | 240° |
| $V_{10}$: | 1.48 V |
| $V_{90}/V_{10}$: | 1.044 |
| $d \cdot \Delta n$: | 0.85 µm |

Example 18

An STN mixture comprising

| | |
|---|---|
| PCH-3N.F.F | 14.00% |
| ME2N.F | 4.00% |
| ME3N.F | 4.00% |
| ME4N.F | 6.00% |
| ME5N.F | 7.00% |
| CC-5-V | 3.00% |
| CCG-V-F | 15.00% |
| CCP-V-1 | 14.00% |
| CVCP-V-1 | 6.00% |
| CVCP-V-O1 | 6.00% |
| CVCP-1V-O1 | 6.00% |
| PTP-102 | 5.00% |
| CPTP-302 | 5.00% |
| CBC-33F | 3.00% |
| CBC-53F | 2.00% |
| Clearing point: | +99.0° C. |
| $\Delta n$: | +0.1404 |
| Twist: | 240° |
| $V_{10}$: | 1.46 V |
| $V_{90}/V_{10}$: | 1.046 |
| $d \cdot \Delta n$: | 0.85 µm |

Example 19

An STN mixture comprising

| | |
|---|---|
| PCH-3N.F.F | 10.00% |
| ME2N.F | 3.00% |
| ME3N.F | 3.00% |
| ME4N.F | 5.00% |
| ME5N.F | 5.00% |
| CC-5-V | 17.00% |
| CCG-V-F | 10.00% |
| CCP-V-1 | 14.00% |
| CVCP-V-1 | 5.00% |
| CVCP-V-O1 | 5.00% |
| CVCP-1V-O1 | 5.00% |
| PTP-102 | 5.00% |
| CPTP-301 | 4.00% |
| CPTP-302 | 5.00% |
| CPTP-303 | 4.00% |
| Clearing point: | +101.0° C. |
| $\Delta n$: | +0.1395 |
| Twist: | 240° |
| $V_{10}$: | 1.77 V |
| $V_{90}/V_{10}$: | 1.059 |
| $d \cdot \Delta n$: | 0.85 µm |

Example 20

An STN mixture comprising

| | |
|---|---|
| PCH-3N.F.F | 14.00% |
| ME2N.F | 4.00% |
| ME3N.F | 4.00% |
| ME4N.F | 6.00% |
| ME5N.F | 6.00% |
| CCG-V-F | 18.50% |
| CCP-V-1 | 16.00% |
| CVCP-V-1 | 5.00% |
| CVCP-V-O1 | 5.00% |
| CVCP-1V-O1 | 5.00% |
| PTP-102 | 5.00% |
| CPTP-301 | 4.50% |
| CBC-33F | 3.00% |
| CBC-53F | 2.00% |
| CBC-55F | 2.00% |
| Clearing point: | +103.0° C. |
| $\Delta n$: | +0.1411 |
| Twist: | 240° |
| $V_{10}$: | 1.49 V |
| $V_{90}/V_{10}$: | 1.051 |
| $d \cdot \Delta n$: | 0.85 µm |

Example 21

An STN mixture comprising

| | |
|---|---|
| PCH-3 | 22.00% |
| PCH-3N.F.F | 20.00% |
| ME2N.F | 1.00% |
| ME3N.F | 1.00% |
| CCG-V-F | 8.00% |
| CCP-V-1 | 15.00% |
| CVCP-V2-1 | 4.00% |
| CVCP-V-1 | 5.00% |
| CVCP-V-C1 | 5.00% |
| CVCP-1V-O1 | 5.00% |
| PTP-102 | 4.00% |
| CPTP-301 | 4.00% |
| CPTP-302 | 4.00% |
| CBC-33 | 2.00% |
| Clearing point: | +93.5° C. |
| $\Delta n$: | +0.1372 |
| Twist: | 240° |
| $V_{10}$: | 1.71 V |
| $V_{90}/V_{10}$: | 1.019 |
| $d \cdot \Delta n$: | 0.85 $\mu$m |

Example 22

An STN mixture comprising

| | |
|---|---|
| CGU-2-F | 8.00% |
| CGU-3-F | 8.00% |
| CCZU-2-F | 5.00% |
| CCZU-3-F | 13.00% |
| CCZU-5-F | 5.00% |
| CCP-3F.F.F | 8.00% |
| CCP-V-1 | 14.00% |
| CVCP-V-O1 | 5.00% |
| CVCP-1V-O1 | 5.00% |
| PGU-3-F | 8.00% |
| PGU-5-F | 8.00% |
| PGU-2-F | 8.00% |
| PPTUI-3-2 | 5.00% |
| Clearing point: | +102.0° C. |
| $\Delta n$: | +0.1429 |
| Twist: | 240° |
| $V_{10}$: | 1.60 V |
| $V_{90}/V_{10}$: | 1.109 |
| $d \cdot \Delta n$: | 0.85 $\mu$m |

Example 23

An STN mixture comprising

| | |
|---|---|
| ME2N.F | 8.00% |
| ME3N.F | 9.00% |
| ME4.N.F | 12.00% |
| PCH-3N.F.F | 13.00% |
| CCG-V-F | 24.00% |
| CVCP-V-1 | 5.00% |
| CVCP-V-O1 | 5.00% |
| CVCP-1V-O1 | 3.00% |
| CCPC-33 | 3.00% |
| CCPC-34 | 2.00% |
| CBC-33 | 3.00% |
| PPTUI-3-2 | 7.00% |
| PPTU-3-4 | 6.00% |
| Clearing point: | +91.0° C. |
| $\Delta n$: | +0.1552 |
| Twist: | 240° |
| $V_{10}$: | 1.14 V |

-continued

| | |
|---|---|
| $V_{90}/V_{10}$: | 1.061 |
| $d \cdot \Delta n$: | 0.85 $\mu$m |

Example 24

An STN mixture comprising

| | |
|---|---|
| PCH-3N.F.F | 10.00% |
| ME2N.F | 6.00% |
| ME3N.F | 6.00% |
| ME4.N.F | 9.00% |
| ME5.N.F | 9.00% |
| CC-5-V | 3.00% |
| CCG-V-F | 15.00% |
| CCP-V-1 | 9.00% |
| CCP-V2-1 | 5.00% |
| CVCP-V-1 | 7.00% |
| CVCP-1V-1 | 8.00% |
| PTP-102 | 3.00% |
| CPTP-301 | 3.00% |
| CBC-33F | 4.00% |
| CBC-53F | 3.00% |
| Clearing point: | +92.0° C. |
| $\Delta n$: | +0.1384 |
| Twist: | 240° |
| $V_{10}$: | 1.28 V |
| $V_{90}/V_{10}$: | 1.037 |
| $d \cdot \Delta n$: | 0.85 $\mu$m |

Example 25

An STN mixture comprising

| | |
|---|---|
| PCH-3 | 27.00% |
| PCH-3N.F.F | 13.00% |
| B-30.FN.F | 10.00% |
| CC-5-V | 2.00% |
| CCP-V-1 | 15.00% |
| CCP-V2-1 | 13.00% |
| CVCP-V-1 | 5.00% |
| CVCP-V-O1 | 5.00% |
| CVCP-1V-O1 | 5.00% |
| CPTP-302 | 3.00% |
| CBC-33 | 2.00% |
| Clearing point: | +91.0° C. |
| $\Delta n$: | +0.1313 |
| Twist: | 240° |
| $V_{10}$: | 1.74 V |
| $V_{90}/V_{10}$: | 1.009 |
| $d \cdot \Delta n$: | 0.85 $\mu$m |

Example 26

An STN mixture comprising

| | |
|---|---|
| ME2N.F | 8.00% |
| ME3N.F | 9.00% |
| ME4.N.F | 12.00% |
| ME5.N.F | 11.00% |
| PCH-3N.F.F | 15.00% |
| CCG-V-F | 9.00% |
| CCP-V-1 | 6.00% |
| CVCP-V-O1 | 5.00% |
| CVCP-1V-O1 | 5.00% |
| CPTP-301 | 2.00% |

-continued

| | |
|---|---|
| CCPC-33 | 5.00% |
| CCPC-34 | 5.00% |
| CCPC-35 | 5.00% |
| CBC-33F | 3.00% |
| Clearing point: | +90.0° C. |
| Δn: | +0.1371 |
| Twist: | 240° |
| $V_{10}$: | 1.02 V |
| $V_{90}/V_{10}$: | 1.022 |
| d · Δn: | 0.85 μm |

Example 27

An STN mixture comprising

| | |
|---|---|
| ME2N.F | 8.00% |
| ME3N.F | 8.00% |
| ME4.N.F | 9.00% |
| ME5.N.F | 9.00% |
| PCH-3N.F.F | 15.00% |
| CCG-V-F | 9.00% |
| CCP-V-1 | 7.00% |
| CVCP-V-O1 | 5.00% |
| CVCP-1V-O1 | 5.00% |
| PPTUI-3-2 | 5.00% |
| CCPC-33 | 5.00% |
| CCPC-34 | 5.00% |
| CCPC-35 | 5.00% |
| CC-5-V | 5.00% |
| Clearing point: | +90.5° C. |
| Δn: | +0.1374 |
| Twist: | 240° |
| $V_{10}$: | 1.10 V |
| $V_{90}/V_{10}$: | 1.023 |
| d · Δn: | 0.85 μm |

Example 28

An STN mixture comprising

| | |
|---|---|
| PCH-3N.F.F | 11.00% |
| ME2N.F | 6.00% |
| ME3N.F | 6.00% |
| ME4.N.F | 9.00% |
| ME5.N.F | 9.00% |
| CCG-V-F | 13.00% |
| CCP-V-1 | 16.00% |
| CVCP-V-1 | 5.00% |
| CVCP-V-O1 | 5.00% |
| CVCP-1V-O1 | 5.00% |
| PTP-102 | 2.00% |
| CPTP-301 | 2.00% |
| CBC-33F | 4.00% |
| CBC-53F | 4.00% |
| CBC-55F | 3.00% |
| Clearing point: | +103.0° C. |
| Δn: | +0.1408 |
| Twist: | 240° |
| $V_{10}$: | 1.28 V |
| $V_{90}/V_{10}$: | 1.030 |
| d · Δn: | 0.85 μm |

Example 29

An STN mixture comprising

| | |
|---|---|
| PCH-3N.F.F | 19.00% |
| ME2N.F | 5.00% |
| ME3N.F | 5.00% |
| ME4.N.F | 9.00% |
| ME5.N.F | 9.00% |
| CCG-V-F | 7.50% |
| CCP-V-1 | 8.00% |
| CVCP-V-1 | 5.00% |
| CVCP-V-O1 | 5.00% |
| CVCP-1V-O1 | 5.00% |
| PTP-102 | 3.00% |
| CPTP-302 | 4.50% |
| CBC-33 | 3.00% |
| CCPC-33 | 4.00% |
| CCPC-34 | 4.00% |
| CCPC-35 | 4.00% |
| Clearing point: | +98.5° C. |
| Δn: | +0.1408 |
| Twist: | 240° |
| $V_{10}$: | 1.23 V |
| $V_{90}/V_{10}$: | 1.032 |
| d · Δn: | 0.85 μm |

Example 30

An STN mixture comprising

| | |
|---|---|
| PCH-3N.F.F | 10.00% |
| ME2N.F | 6.00% |
| ME3N.F | 6.00% |
| ME4.N.F | 9.00% |
| ME5.N.F | 9.00% |
| CC-5-V | 3.00% |
| CCG-V-F | 15.00% |
| CCP-V-1 | 9.00% |
| CVCP-V2-1 | 5.00% |
| CVCP-V-O1 | 7.00% |
| CVCP-1V-O1 | 8.00% |
| PTP-102 | 3.00% |
| CPTP-301 | 3.00% |
| CBC-33F | 4.00% |
| CBC-53F | 3.00% |
| Clearing poiflt: | +98.0° C. |
| Δn: | +0.1405 |
| Twist: | 240° |
| $V_{10}$: | 1.32 V |
| $V_{90}/V_{10}$: | 1.051 |
| d · Δn: | 0.85 μm |

Example 31

An STN mixture comprising

| | |
|---|---|
| PCH-3N.F.F | 20.00% |
| ME2N.F | 5.00% |
| ME3N.F | 5.00% |
| ME4.N.F | 9.00% |
| ME5.N.F | 9.00% |
| CCG-V-F | 7.00% |
| CCP-V-1 | 8.00% |
| CVCP-V-1 | 5.00% |
| CVCP-V-O1 | 5.00% |
| CVCP-1V-O1 | 5.00% |
| PPTUI-3-2 | 5.50% |
| CBC-33 | 2.50% |
| CCPC-33 | 5.00% |

| | |
|---|---|
| CCPC-34 | 5.00% |
| CCPC-35 | 4.00% |
| Clearing point: | +98.0° C. |
| Δn: | +0.1403 |
| Twist: | 240° |
| $V_{10}$: | 1.20 V |
| $V_{90}/V_{10}$: | 1.045 |
| d · Δn: | 0.85 μm |

Example 32

An STN mixture comprising

| | |
|---|---|
| PCH-3N.F.F | 14.00% |
| ME2N.F | 4.00% |
| ME3N.F | 4.00% |
| ME4.N.F | 7.00% |
| ME5.N.F | 7.00% |
| CC-5-V | 3.00% |
| CCG-V-F | 15.00% |
| CCP-V-1 | 14.00% |
| CVCP-V-1 | 6.00% |
| CVCP-V-O1 | 6.00% |
| CVCP-IV-O1 | 6.00% |
| PPTUI-3-2 | 6.50% |
| CBC-33F | 4.00% |
| CBC-53F | 3.50% |
| Clearing point: | +101.5° C. |
| Δn: | +0.1400 |
| Twist: | 240° |
| $V_{10}$: | 1.44 V |
| $V_{90}/V_{10}$: | 1.040 |
| d · Δn: | 0.85 μm |

Example 33

An STN mixture comprising

| | |
|---|---|
| PCH-3N.F.F | 10.00% |
| ME2N.F | 3.00% |
| ME3N.F | 3.00% |
| ME4.N.F | 6.00% |
| ME5.N.F | 6.00% |
| CC-5-V | 18.00% |
| CCG-V-F | 7.00% |
| CCP-V-1 | 13.00% |
| CVCP-V-1 | 5.00% |
| CVCP-V-O1 | 5.00% |
| CVCP-1V-O1 | 5.00% |
| PPTUI-3-2 | 12.50% |
| CCPC-33 | 2.50% |
| CCPC-34 | 2.00% |
| CCPC-35 | 2.00% |
| Clearing point: | +104.5° C. |
| Δn: | +0.1402 |
| Twist: | 240° |
| $V_{10}$: | 1.71 V |
| $V_{90}/V_{10}$: | 1.049 |
| d · Δn: | 0.85 μm |

Example 34

An STN mixture comprising

| | |
|---|---|
| PCH-3 | 27.00% |
| PCH-3N.F.F | 23.00% |
| CC-5-V | 2.00% |
| CCP-V-1 | 15.00% |
| CCP-V2-1 | 6.00% |
| CVCP-V-1 | 5.00% |
| CVCP-V-O1 | 5.00% |
| CVCP-1V-O1 | 5.00% |
| CPTP-301 | 5.00% |
| CPTP-302 | 5.00% |
| CBC-33 | 2.00% |
| Clearing point: | +90.5° C. |
| Δn: | +0.1324 |
| Twist: | 240° |
| $V_{10}$: | 1.73 V |
| $V_{90}/V_{10}$: | 1.023 |
| d · Δn: | 0.85 μm |

Example 35

An STN mixture comprising

| | |
|---|---|
| PCH-3 | 22.00% |
| PCH-3N.F.F | 20.00% |
| ME2N.F | 2.00% |
| ME3N.F | 1.00% |
| CC-5-V | 1.00% |
| CCG-V-F | 8.00% |
| CCP-V-1 | 15.00% |
| CCP-V2-1 | 4.00% |
| CVCP-V-1 | 5.00% |
| CVCP-V-O1 | 5.00% |
| CVCP-1V-O1 | 5.00% |
| PTP-102 | 3.00% |
| CPTP-302 | 5.00% |
| CBC-33 | 4.00% |
| Clearing point: | +92.0° C. |
| Δn: | +0.1312 |
| Twist: | 240° |
| $V_{10}$: | 1.70 V |
| $V_{90}/V_{10}$: | 1.023 |
| d · Δn: | 0.85 μm |

Example 36

An STN mixture comprising

| | |
|---|---|
| PCH-3N.F.F | 17.00% |
| ME2N.F | 2.00% |
| ME3N.F | 3.00% |
| ME4N.F | 7.00% |
| CC-3-V1 | 10.00% |
| CC-5-V | 10.00% |
| CVCP-1V-O1 | 4.00% |
| CVCP-V-O1 | 4.00% |
| CVCP-V-1 | 4.00% |
| CCP-V-1 | 16.00% |
| CCP-V2-1 | 16.00% |
| PPTUI-3-2 | 7.00% |
| Clearing point: | +95.0° C. |
| Δn: | +0.1226 |
| Twist: | 240° |
| $V_{10}$: | 1.85 V |
| $V_{90}/V_{10}$: | 1.050 |
| d · Δn: | 0.85 μm |

Example 37

An STN mixture comprising

| | |
|---|---|
| ME2N.F | 4.00% |
| ME3N.F | 4.00% |
| ME4N.F | 12.00% |
| PCH-3N.F.F | 10.00% |
| CC-5-V | 3.00% |
| CC-3-V1 | 8.00% |
| CCP-V-1 | 16.00% |
| CCP-V2-1 | 16.00% |
| CVCP-V-O1 | 5.00% |
| CVCP-V-1 | 5.00% |
| PPTUI-3-2 | 7.00% |
| CBC-33F | 5.00% |
| CBC-53F | 5.00% |
| Clearing point: | +116.0° C. |
| Δn: | +0.1404 |
| Twist: | 240° |
| $V_{10}$: | 1.73 V |
| $V_{90}/V_{10}$: | 1.051 |
| d · Δn: | 0.85 μm |

Example 38

An STN mixture comprising.

| | |
|---|---|
| ME2N.F | 2.00% |
| ME3N.F | 3.00% |
| ME4N.F | 9.00% |
| PCH-3N.F.F | 12.50% |
| CC-5-V | 3.50% |
| CC-3-V1 | 9.00% |
| CCP-V-1 | 16.00% |
| CCP-V2-1 | 16.00% |
| CVCP-V-O1 | 5.00% |
| CVCP-V-1 | 5.00% |
| PPTUI-3-2 | 9.00% |
| CBC-33F | 5.00% |
| CBC-53F | 5.00% |
| Clearing point: | +120.0° C. |
| Δn: | +0.1407 |
| Twist: | 240° |
| $V_{10}$: | 1.97 V |
| $V_{90}/V_{10}$: | 1.047 |
| d · Δn: | 0.85 μm |

Example 39

An STN mixture comprising

| | |
|---|---|
| ME2N.F | 4.00% |
| ME3N.F | 4.00% |
| ME4N.F | 12.00% |
| PCH-3N.F.F | 22.00% |
| PCH-3 | 5.00% |
| CC-3-V1 | 2.00% |
| CCG-V-F | 9.00% |
| CCP-V-1 | 8.50% |
| CVCP-V-O1 | 5.00% |
| CVCP-1V-O1 | 5.00% |
| CVCP-V-1 | 5.00% |
| CPTP-301 | 5.50% |
| CPTP-302 | 2.00% |
| CBC-33F | 5.50% |
| CBC-53F | 5.50% |
| Clearing point: | +92.0° C. |
| Δn: | +0.1374 |
| Twist: | 240° |
| $V_{10}$: | 1.29 V |
| $V_{90}/V_{10}$: | 1.040 |
| d · Δn: | 0.85 μm |

Example 40

An STN mixture comprising

| | |
|---|---|
| ME2N.F | 2.00% |
| ME3N.F | 3.00% |
| ME4N.F | 3.00% |
| PCH-3N.F.F | 11.00% |
| PCH-3 | 25.00% |
| CVCP-V-O1 | 4.00% |
| CVCP-1V-O1 | 4.00% |
| CC-3-V1 | 5.00% |
| CCP-V-1 | 14.00% |
| CCP-V2-1 | 14.00% |
| CCG-V-F | 5.00% |
| PPTUI-3-2 | 10.00% |
| Clearing point: | +92.0° C. |
| Δn: | +0.1417 |
| Twist: | 240° |
| $V_{10}$: | 1.71 V |
| $V_{90}/V_{10}$: | 1.042 |
| d · Δn: | 0.85 μm |

Example 41

An STN mixture comprising

| | |
|---|---|
| ME2N.F | 4.00% |
| ME3N.F | 4.00% |
| ME4N.F | 12.00% |
| PCH-3N.F.F | 18.50% |
| PCH-3 | 8.50% |
| CC-3-V1 | 2.00% |
| CCG-V-F | 9.00% |
| CCP-V-1 | 9.00% |
| CVCP-V-O1 | 5.00% |
| CVCP-1V-O1 | 5.00% |
| CVCP-V-1 | 5.00% |
| CPTP-301 | 6.00% |
| CBC-33F | 6.00% |
| CBC-53F | 6.00% |
| Clearing point: | +95.0° C. |
| Δn: | +0.1372 |
| Twist: | 240° |
| $V_{10}$: | 1.34 V |
| $V_{90}/V_{10}$: | 1.037 |
| d · Δn: | 0.85 μm |

Example 42

An STN mixture comprising

| | |
|---|---|
| PCH-3N.F.F | 16.00% |
| ME2N.F | 2.00% |
| ME3N.F | 3.00% |
| ME4.N.F | 6.00% |
| CC-3-V1 | 8.00% |
| CC-5-V | 13.00% |
| CVCP-1V-O1 | 4.00% |
| CVCP-V-1 | 4.00% |
| CCP-V-1 | 16.00% |

-continued

| | |
|---|---|
| CCP-V2-1 | 16.00% |
| CCG-V-F | 5.00% |
| PPTUI-3-2 | 7.00% |
| Clearing point: | +95.0° C. |
| Δn: | +0.1193 |
| Twist: | 240° |
| $V_{10}$: | 1.86 V |
| $V_{90}/V_{10}$: | 1.055 |
| d · Δn: | 0.85 μm |

Example 43

An STN mixture comprising

| | |
|---|---|
| ME2N.F | 8.00% |
| ME3N.F | 8.00% |
| ME4.N.F | 14.50% |
| PCH-3 | 16.00% |
| CC-3-V1 | 3.50% |
| CCG-V-F | 18.00% |
| CCP-V-1 | 7.00% |
| CVCP-V-O1 | 5.00% |
| CVCP-1V-O1 | 5.00% |
| CVCP-V-1 | 5.00% |
| CPTP-301 | 2.00% |
| CBC-33F | 4.00% |
| CBC-53F | 4.00% |
| Clearing point: | +95.0° C. |
| Δn: | +0.1371 |
| Twist: | 240° |
| $V_{10}$: | 1.34 V |
| $V_{90}/V_{10}$: | 1.029 |
| d · Δn: | 0.85 μm |

Example 44

An STN mixture comprising

| | |
|---|---|
| ME2N.F | 8.00% |
| ME3N.F | 8.00% |
| ME4.N.F | 16.00% |
| PCH-3 | 10.00% |
| CC-3-V1 | 8.00% |
| CCG-V-F | 18.00% |
| CCP-V-1 | 8.50% |
| CVCP-V-O1 | 5.00% |
| CVCP-1V-O1 | 5.00% |
| CVCP-V-1 | 5.00% |
| CPTP-301 | 4.50% |
| CBC-33F | 4.00% |
| Clearing point: | +95.0° C. |
| Δn: | +0.1364 |
| Twist: | 240° |
| $V_{10}$: | 1.34 V |
| $V_{90}/V_{10}$: | 1.037 |
| d · Δn: | 0.85 μm |

Example 45

An STN mixture comprising

| | |
|---|---|
| ME2N.F | 8.00% |
| ME3N.F | 8.00% |
| ME4.N.F | 16.00% |
| PCH-3 | 7.00% |

-continued

| | |
|---|---|
| CC-5-V | 2.00% |
| CC-3-V1 | 8.00% |
| CCG-V-F | 18.00% |
| CCP-V-1 | 11.00% |
| CVCP-V-O1 | 5.00% |
| CVCP-1V-O1 | 5.00% |
| CVCP-V-1 | 5.00% |
| CPTP-301 | 5.00% |
| CPTP-301 | 2.00% |
| Clearing point: | +95.0° C. |
| Δn: | +0.1364 |
| Twist: | 240° |
| $V_{10}$: | 1.35 V |
| $V_{90}/V_{10}$: | 1.041 |
| d · Δn: | 0.85 μm |

Example 46

An STN mixture comprising

| | | | |
|---|---|---|---|
| ME2N.F | 2.00% | Clearing point: | +95.0° C. |
| ME3N.F | 3.00% | Δn: | +0.1450 |
| ME4.N.F | 4.00% | Twist: | 240° |
| PCH-3N.F.F | 11.00% | $V_{10}$: | 1.72 V |
| PCH-3 | 25.00% | $V_{90}/V_{10}$: | 1.038 |
| CVCP-V-O1 | 4.00% | d · Δn: | 0.85 μm |
| CVCP-1V-O1 | 4.00% | | |
| CVCP-V-1 | 16.00% | | |
| CVCP-V2-1 | 16.00% | | |
| CCG-V-F | 5.00% | | |
| PPTUI-3-2 | 10.00% | | |

Example 47

An STN mixture comprising

| | | | |
|---|---|---|---|
| ME2N.F | 2.00% | Clearing point: | +90.0° C. |
| ME3N.F | 3.00% | Δn: | +0.1407 |
| ME4.N.F | 6.00% | Twist: | 240° |
| PCH-3N.F.F | 15.00% | $V_{10}$: | 1.56 V |
| PCH-3 | 19.00% | $V_{90}/V_{10}$: | 1.039 |
| CVCP-V-O1 | 4.00% | d · Δn: | 0.85 μm |
| CVCP-1V-O1 | 4.00% | | |
| CVCP-V-1 | 16.00% | | |
| CVCP-V2-1 | 16.00% | | |
| CCG-V-F | 6.00% | | |
| PPTUI-3-2 | 9.00% | | |

Example 48

An STN mixture comprising

| | | | |
|---|---|---|---|
| ME2N.F | 8.00% | Clearing point: | +95.0° C. |
| ME3N.F | 8.00% | Δn: | +0.1378 |
| ME4.N.F | 16.00% | Twist: | 240° |
| PCH-3N.F.F | 2.00% | $V_{10}$: | 1.33 V |
| PCH-3 | 10.00% | $V_{90}/V_{10}$: | 1.036 |
| PCH-301 | 6.00% | d · Δn: | 0.85 μm |
| CCG-V-F | 9.00% | | |
| CCP-V-1 | 16.00% | | |
| CVCP-V-O1 | 5.00% | | |
| CVCP-1V-O1 | 5.00% | | |
| CVCP-V-1 | 5.00% | | |

-continued

| | |
|---|---|
| CPTP-301 | 2.00% |
| CBC-33F | 4.00% |
| CBC-53F | 4.00% |

Example 49

An STN mixture comprising

| | | | |
|---|---|---|---|
| ME2N.F | 5.00% | Clearing point: | +77.0° C. |
| ME3N.F | 5.00% | Δn: | +0.1421 |
| ME4.N.F | 6.00% | Twist: | 240° |
| PCH-3N.F.F | 17.00% | $V_{10}$: | 1.37 V |
| PCH-3 | 9.00% | $V_{90}/V_{10}$: | 1.051 |
| CC-3-V1 | 8.00% | d · Δn: | 0.85 μm |
| CCG-V-F | 10.00% | | |
| CCP-V-1 | 13.50% | | |
| CVCP-V-O1 | 5.00% | | |
| CVCP-1V-O1 | 5.00% | | |
| PTP-102 | 5.50% | | |
| PTP-201 | 3.00% | | |
| CPTP-301 | 5.50% | | |
| CPTP-302 | 2.50% | | |

Example 50

An STN mixture comprising

| | | | |
|---|---|---|---|
| ME2N.F | 5.00% | Clearing point: | +77.0° C. |
| ME3N.F | 5.00% | Δn: | +0.1440 |
| ME4.N.F | 6.00% | Twist: | 240° |
| PCH-3N.F.F | 17.00% | $V_{10}$: | 1.38 V |
| PCH-3 | 9.00% | $V_{90}/V_{10}$: | 1.045 |
| CCG-V-F | 10.00% | d · Δn: | 0.85 μm |
| CVC-3-V | 5.00% | | |
| CVC-3-V1 | 5.00% | | |
| CVCP-1V-1 | 5.00% | | |
| CVCP-V-O1 | 5.00% | | |
| CVCP-1V-O1 | 5.00% | | |
| PTP-102 | 5.50% | | |
| PTP-201 | 3.00% | | |
| CPTP-301 | 5.50% | | |
| CPTP-302 | 4.00% | | |
| CVCP-V-1 | 5.00% | | |

Example 51

An STN mixture comprising

| | | | |
|---|---|---|---|
| ME2N.F | 2.50% | Clearing point: | +122.0° C. |
| ME3N.F | 3.50% | Δn: | +0.1446 |
| ME4.N.F | 8.50% | Twist: | 240° |
| CC-5-V | 13.50% | $V_{10}$: | 2.37 V |
| CCG-V-F | 15.00% | $V_{90}/V_{10}$: | 1.043 |
| CCP-V-1 | 15.00% | d · Δn: | 0.85 μm |
| CCP-V2-1 | 15.00% | | |
| CVCP-V-1 | 4.50% | | |
| CVCP-1V-1 | 4.00% | | |
| CVCP-1V-O1 | 4.50% | | |
| PPTUI-3-2 | 14.00% | | |

Example 52

An STN mixture comprising

| | | | |
|---|---|---|---|
| ME2N.F | 2.50% | Clearing point: | +118.0° C. |
| ME3N.F | 3.50% | Δn: | +0.1405 |
| ME4.N.F | 9.00% | Twist: | 240° |
| CC-5-V | 15.00% | $V_{10}$: | 2.31 V |
| CCG-V-F | 16.00% | $V_{90}/V_{10}$: | 1.051 |
| CCP-V-1 | 15.50% | d · Δn: | 0.85 μm |
| COP-V2-1 | 15.50% | | |
| CVCP-V-1 | 5.00% | | |
| CVCP-1V-1 | 5.00% | | |
| PPTUI-3-2 | 13.00% | | |

Example 53

An STN mixture comprising

| | | | |
|---|---|---|---|
| ME2N.F | 4.00% | Clearing point: | +95.0° C. |
| ME3N.F | 4.00% | Δn: | +0.1715 |
| ME4.N.F | 10.00% | Twist: | 240° |
| PCH-3N.F.F | 19.00% | $V_{10}$: | 1.43 V |
| CC-5-V | 11.00% | $V_{90}/V_{10}$: | 1.076 |
| CVCP-1V-O1 | 4.00% | d · Δn: | 0.85 μm |
| CVCP-1V-1 | 4.00% | | |
| CCP-V-1 | 13.00% | | |
| CBC-33F | 5.00% | | |
| CBC-53F | 4.00% | | |
| PPTUI-3-2 | 22.00% | | |

Example 54

An STN mixture comprising

| | | | |
|---|---|---|---|
| ME2N.F | 4.00% | Clearing point: | +97.0° C. |
| ME3N.F | 4.00% | Δn: | +0.1733 |
| ME4.N.F | 10.00% | Twist: | 240° |
| PCH-3N.F.F | 18.00% | $V_{10}$: | 1.44 V |
| CC-5-V | 11.50% | $V_{90}/V_{10}$: | 1.069 |
| CVCP-1V-O1 | 4.00% | d · Δn: | 0.85 μm |
| CVCP-1V-1 | 4.00% | | |
| CCP-V-1 | 13.00% | | |
| CBC-33F | 5.00% | | |
| CBC-53F | 4.00% | | |
| PPTUI-3-2 | 22.50% | | |

Example 55

An STN mixture comprising

| | | | |
|---|---|---|---|
| ME2N.F | 4.00% | Clearing point: | +97.0° C. |
| ME3N.F | 4.00% | Δn: | +0.1735 |
| ME4.N.F | 10.00% | Twist: | 240° |
| PCH-3N.F.F | 18.00% | $V_{10}$: | 1.46 V |
| CC-5-V | 11.00% | $V_{90}/V_{10}$: | 1.073 |
| CVCP-1V-O1 | 4.00% | d · Δn: | 0.85 μm |
| CVCP-1V-1 | 4.00% | | |
| CCP-V-1 | 13.50% | | |
| CBC-33F | 5.00% | | |
| CBC-53F | 4.00% | | |
| PPTUI-3-2 | 22.50% | | |

Example 56

An STN mixture comprising

| | | | |
|---|---|---|---|
| ME2N.F | 4.00% | Clearing point: | +97.0° C. |
| ME3N.F | 4.00% | Δn: | +0.1732 |
| ME4.N.F | 10.00% | Twist: | 240° |
| PCH-3N.F.F | 18.00% | $V_{10}$: | 1.46 V |
| CC-5-V | 11.00% | $V_{90}/V_{10}$: | 1.073 |
| CVCP-1V-O1 | 4.00% | d · Δn: | 0.85 μm |
| CVCP-1V-1 | 4.00% | | |
| CCP-V-1 | 12.50% | | |
| CBC-33F | 5.00% | | |
| CBC-53F | 5.00% | | |
| PPTUI-3-2 | 22.50% | | |

Example 57

An STN mixture comprising

| | | | |
|---|---|---|---|
| PCH-3N.F.F | 19.00% | Clearing point: | +95.0° C. |
| ME2N.F | 4.00% | Δn: | +0.1417 |
| ME3N.F | 4.00% | Twist: | 240° |
| ME4.N.F | 10.50% | $V_{10}$: | 1.46 V |
| CC-3-V1 | 7.00% | $V_{90}/V_{10}$: | 1.038 |
| CVCP-1V-O1 | 4.50% | d · Δn: | 0.85 μm |
| CVCP-V-O1 | 4.50% | | |
| CVCP-1V-1 | 4.50% | | |
| CCP-V-1 | 16.00% | | |
| CCP-V2-1 | 16.00% | | |
| PPTUI-3-2 | 10.00% | | |

What is claimed is:

1. A supertwist liquid-crystal display comprising:

two outer plates which, together with a frame, form a cell, a nematic liquid-crystal mixture of positive dielectric anisotropy which is present in the cell, electrode layers with alignment layers on the insides of the outer plates, a pre-tilt angle between the longitudinal axis of the molecules at the surface of the outer plates and the outer plates of from about 0 degrees to 30 degrees, and a twist angle of the liquid-crystal mixture in the cell from alignment layer to alignment layer with a value of from 22.5° to 600°, wherein the nematic liquid-crystal mixture comprises:
   a) 15–90% by weight of a liquid-crystalline component A consisting of one or more compounds having a dielectric anisotropy of greater than +1.5;
   b) 0–60% by weight of a liquid-crystalline component B consisting of one or more compounds having a dielectric anisotropy of between −1.5 and +1.5;
   c) 0–20% by weight of a liquid-crystalline component D consisting of one or more compounds having a dielectric anisotropy of below −1.5, and
   d) optionally, an optically active component C in such an amount that the ratio between the layer thickness (separation of the outer plates) and the natural pitch of the chiral nematic liquid-crystal mixture is from about 0.2 to 1.3, wherein the liquid-crystal mixture comprises at least one compound of the formula IA

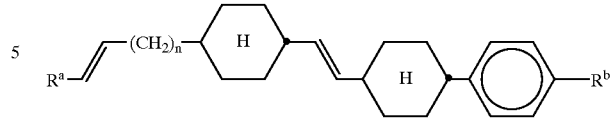

IA in which $R^a$ is H or an alkyl group having 1 to 7 carbon atoms,
$R^b$ is an alkyl or alkoxy group having 1 to 10 carbon atoms or an alkenyl or alkenyloxy group having 2 to 10 carbon atoms,
and
n is 0, 1 or 2, and simultaneously comprises at least one compound of the formulae IB1 to IB4:

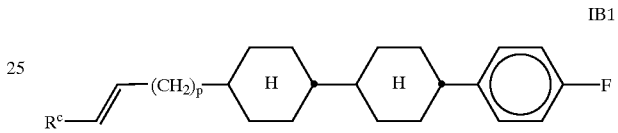

IB1

IB2

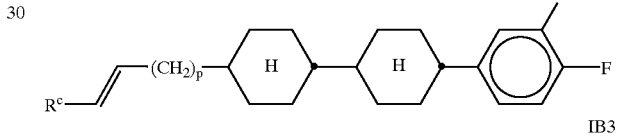

IB3

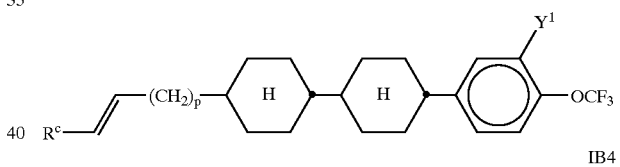

IB4

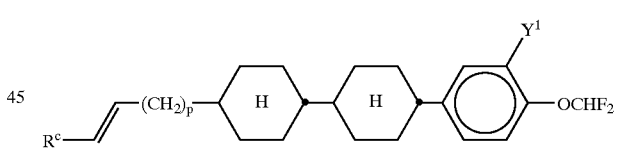

in which $R^c$ is H or an alkyl group having 1 to 7 carbon atoms,
$Y^1$ is H or F,
and
p is 0, 1 or 2.

2. A liquid-crystal display according to claim 1, wherein the liquid-crystal mixture comprises at least one compound of the formula IA in which $R^b$ is a straight-chain alkoxy group having 1 to 7 carbon atoms.

3. A liquid-crystal display according to claim 1, wherein the liquid-crystal mixture further comprises at least one compound of at least one of the following formulae IB5 to IB7:

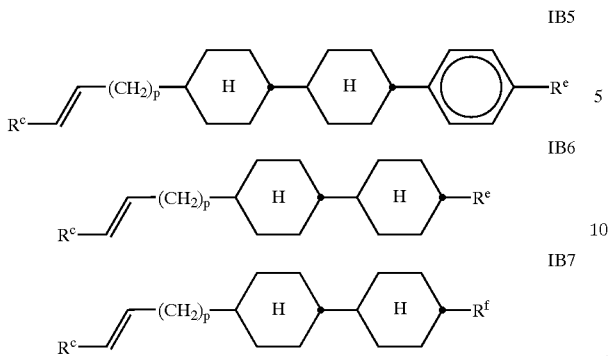

IB5

IB6

IB7 in which $R^c$, $Y^1$, and p are as defined in claim 1,

| $R^e$ | is an alkyl or alkoxy group having 1 to 7 carbon atoms, and |
| $R^f$ | is an alkenyl group having 2 to 7 carbon atoms. |

4. A liquid-crystal display according to claim 1, wherein Component A additionally comprises at least one compound of the formulae II and/or III.

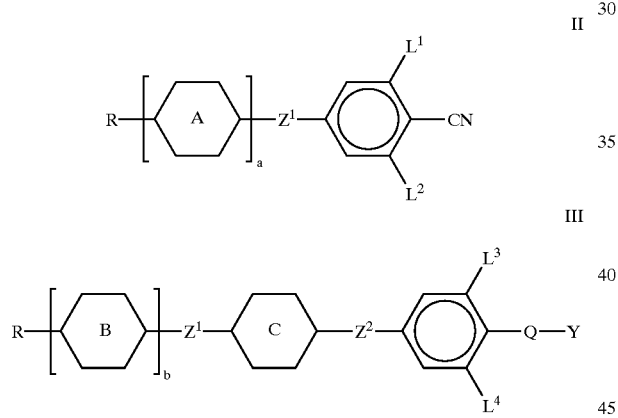

II

III in which

| R | is an alkyl, alkoxy or alkenyl group having 1 to 12 carbon atoms, in which, in addition, one or two non-adjacent $CH_2$ groups are optionally replaced by —O—, —CH=CH—, —CO—, —OCO— or —COO— in such a way that O atoms are not linked directly to one another, |

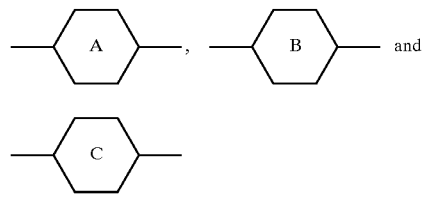

are each, independently of one another

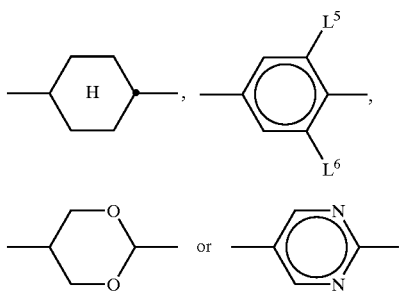

$L^1$ to $L^6$ are each, independently of one another, H or F,
$Z^1$ is —COO—, —$CH_2CH_2$— or a single bond,
$Z^2$ is —$CH_2CH_2$—, —COO—, —C≡C— or a single bond,
Q is —$CF_2$—, —CHF—, —$OCF_2$—, —OCHF— or a single bond,
Y is F or Cl,
a is 1 or 2, and
b is 0 or 1, where compounds of the formulae IB1 to IB4 are excluded from the scope of the formula III.

5. A liquid-crystal display according to claim 1, wherein Component A comprises at least one compound of at least one of the following formulae:

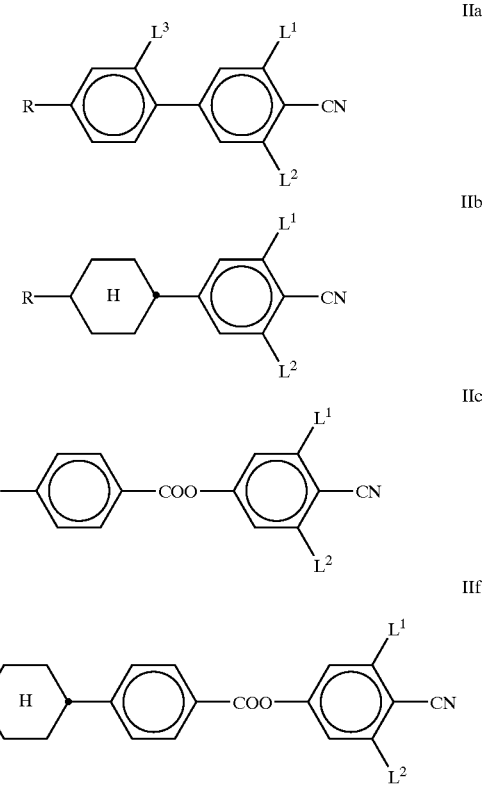

in which R is an alkyl, alkoxy or alkenyl group having 1 to 12 carbon atoms, in which, in addition, one or two non-adjacent $CH_2$ groups are optionally replaced by —O—, —CH=CH—, —CO—, —OCO— or —COO— in such a way that O atoms are not linked directly to one another, and $L^1$, $L^2$ and $L^3$ are each independently of one another H or F.

6. A liquid-crystal display according to claim 1, wherein Component A comprises one or more compounds of the following formula:

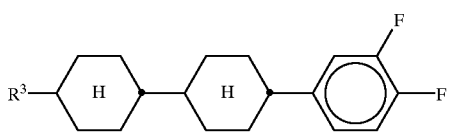

IIIb1 in which $R^3$ is alkyl or alkoxy having 1 to 7 carbon atoms.

7. A liquid-crystal display according to claim 1, wherein Component A comprises one or more compounds of at least one of the following formulae:

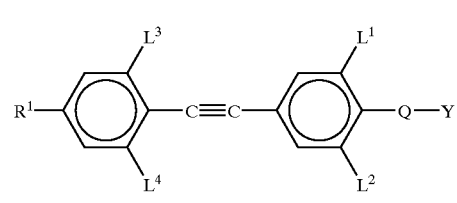

T1a

T1b in which $L^1$ to $L^4$ are H or F, Q—Y is F, Cl or $OCF_3$, and $R^1$ is an alkyl, alkoxy or alkenyl group having 1 to 12 carbon atoms, in which, in addition, one or two non-adjacent $CH_2$ groups are optionally replaced by —O—, —CH=CH—, —CO—, —OCO— or —COO— in such a way that O atoms are not linked directly to one another.

8. A liquid-crystal display according to claim 1, wherein Component B comprises one or more compounds selected from the group consisting of compounds of the formulae T2a to T2e:

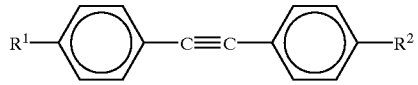

T2a

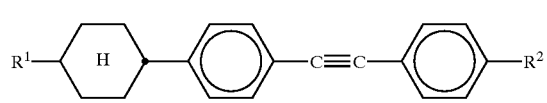

T2b

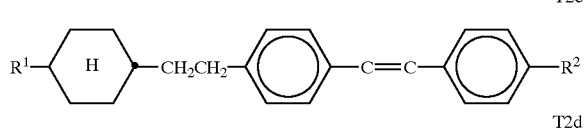

T2c

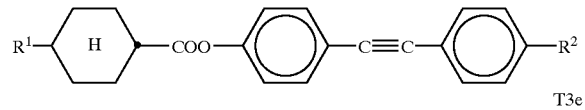

T2d

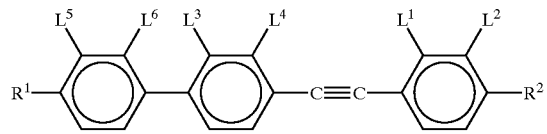

T3e in which $R^1$ and $R^2$ are an alkyl, alkoxy or alkenyl group having 1 to 12 carbon atoms, in which, in addition, one or two non-adjacent $CH_2$ groups are optionally replaced by —O—, —CH=CH—, —CO—, —OCO— or —COO— in such a way that O atoms are not linked directly to one another, and one, two or three of the radicals $L^1$ to $L^6$ are F and the others are H, where $L^1$ and $L^2$ or $L^3$ and $L^4$ or $L^5$ and $L^6$ are not both simultaneously F.

9. A liquid-crystal display according to claim 1, wherein Component B comprises one or more compounds selected from the group consisting of compounds of the formulae T3a to T3e:

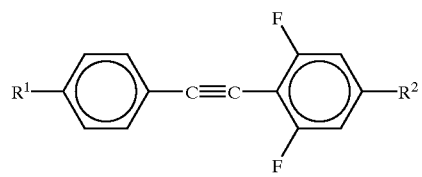

T3a

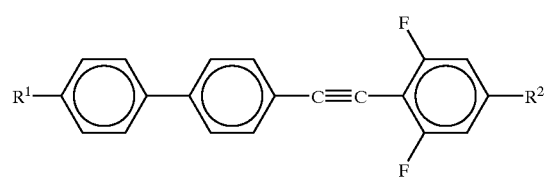

T3b

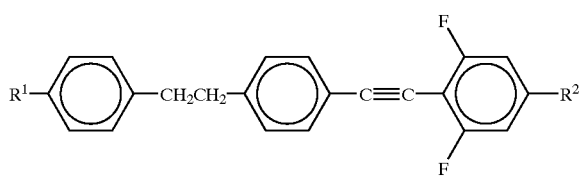

T3c

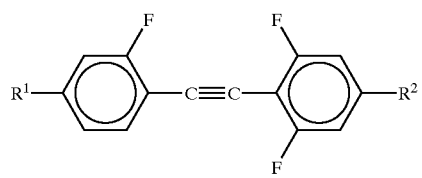

T3d

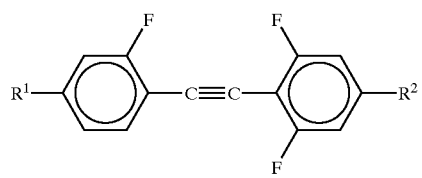

T3e in which $R^1$ and $R^2$ are an alkyl, alkoxy or alkenyl group having 1 to 12 carbon atoms, in which, in addition, one or two non-adjacent $CH_2$ groups are optionally replaced by —O—, —CH=CH—, —CO—, —OCO— or —COO— in such a way that O atoms are not linked directly to one another, and $Z^4$ is —CO—O—, —$CH_2CH_2$— or a single bond.

10. A liquid-crystal display according to claim 1, wherein Component B additionally comprises one or more compounds of at least one of the formulae IV25 to IV31:

IV25

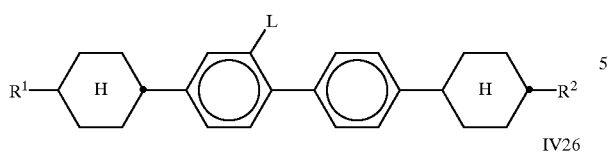

IV26

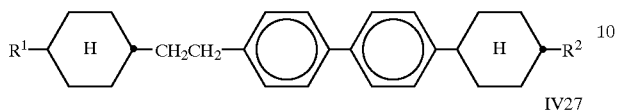

IV27

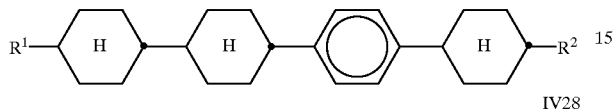

IV28

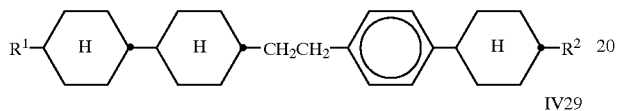

IV29

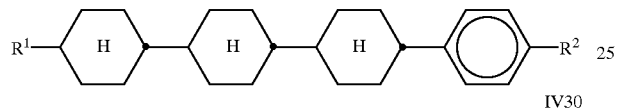

IV30

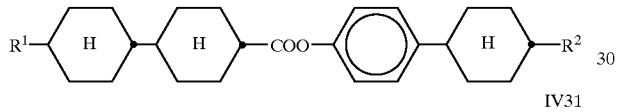

IV31

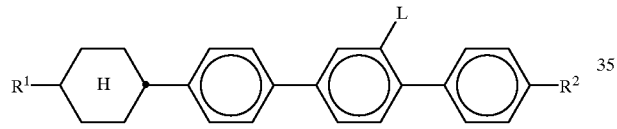

in which $R^1$ and $R^2$ are each, independently of one another, are an alkyl, alkoxy or alkenyl group having 1 to 12 carbon atoms, in which, in addition, one or two non-adjacent $CH_2$ groups are optionally replaced by —O—, —CH=CH—, —CO—, —OCO— or —COO— in such a way that O atoms are not linked directly to one another, and L is H or F.

11. A liquid-crystal display according to claim 1, wherein Component B additionally comprises one or more compounds of at least one of the formulae IV1 to IV24:

IV1

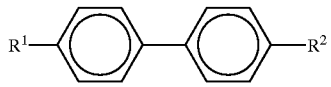

IV2

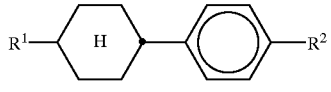

IV3

IV4

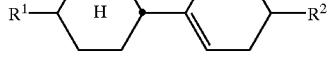

IV5

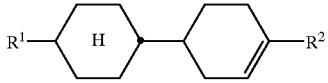

IV6

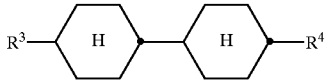

IV7

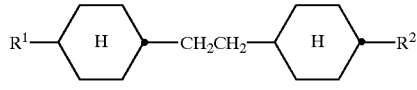

IV8

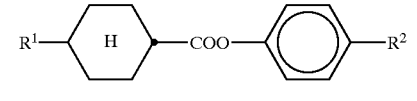

IV9

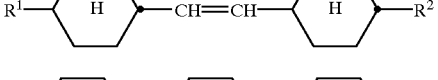

IV10

IV11

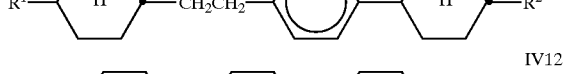

IV12

IV13

IV14

IV15

IV16

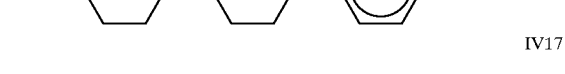

IV17

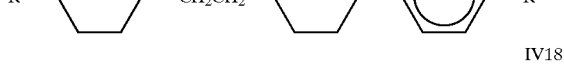

IV18

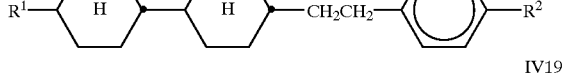

IV19

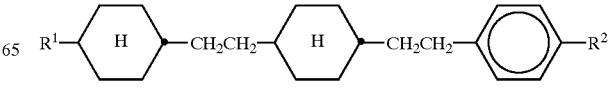

-continued

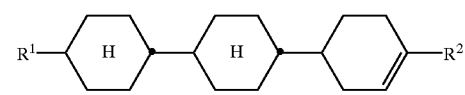
IV20

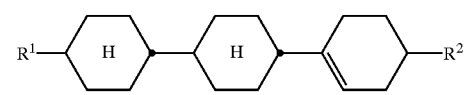
IV21

IV22

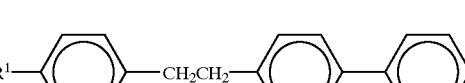
IV23

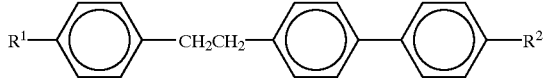
IV24 in which $R^1$ and $R^2$ are each, independently of one another, are is an alkyl, alkoxy or alkenyl group having 1 to 12 carbon atoms, in which, in addition, one or two non-adjacent $CH_2$ groups are optionally replaced by —O—, —CH=CH—, —CO—, —OCO— or —COO— in such a way that O atoms are not linked directly to one another, and $R^3$ and $R^4$ are an alkyl or alkoxy group having 1 to 7 carbon atoms.

12. A liquid-crystal mixture comprising:
 a) 15–90% by weight of a liquid-crystalline component A consisting of one or more compounds having a dielectric anisotropy of greater than +1.5;
 b) 0–60% by weight of a liquid-crystalline component B consisting of one or more compounds having a dielectric anisotropy of between −1.5 and +1.5;
 c) 0–20% by weight of a liquid-crystalline component D consisting of one or more compounds having a dielectric anisotropy of below −1.5, and
 d) optionally, an optically active component C in such an amount that the ratio between the layer thickness (separation of the outer plates) and the natural pitch of the chiral nematic liquid-crystal mixture is from about 0.2 to 1.3, and further comprising at least one compound of the formula IA

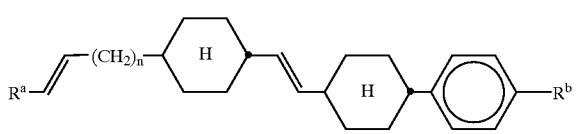
IA in which

| | |
|---|---|
| $R^a$ | is H or an alkyl group having 1 to 7 carbon atoms, |
| $R^b$ | is an alkyl or alkoxy group having 1 to 10 carbon atoms or an alkenyl or alkenyloxy group having 2 to 10 carbon atoms, |
| and | |
| n | is 0, 1 or 2 | and simultaneously comprises at least one compound of the formula IB

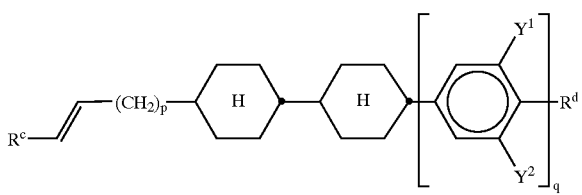
IB in which

| | |
|---|---|
| $R^c$ | is H or an alkyl group having 1 to 7 carbon atoms, |
| $R^d$ | is F, $OCF_3$, $OCHF_2$, an alkyl or alkoxy group having 1 to 7 carbon atoms or an alkenyl group having 2 to 7 carbon atoms, |
| $Y^1$ and $Y^2$, | independently of one another, are H or F, |
| q | is 0 or 1 |
| and | |
| p | is 0, 1 or 2. |

13. A liquid-crystal display according to claim 3, wherein Component A additionally comprises at least one compound of the formulae II and/or III:

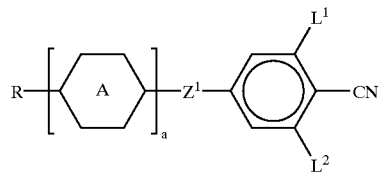
II

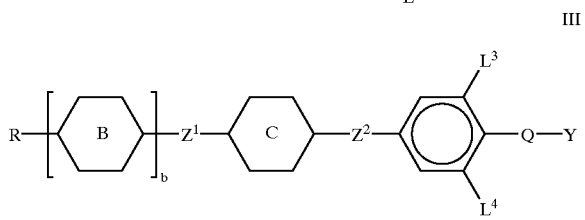
III in which

R is an alkyl, alkoxy or alkenyl group having 1 to 12 carbon atoms, in which, in addition, one or two non-adjacent $CH_2$ groups are optionally replaced by —O—, —CH=CH—, —CO—, —OCO— or —COO— in such a way that O atoms are not linked directly to one another,

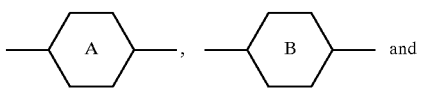 and

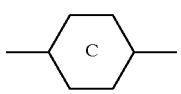

are each, independently of one another

-continued

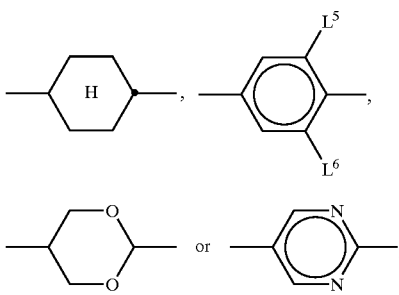

| | |
|---|---|
| L¹ to L⁶ | are each, independently of one another, H or F, |
| Z¹ | is —COO—, —CH₂CH₂— or a single bond, |
| Z² | is —CH₂CH₂—, —COO—, —C≡C— or a single bond, |
| Q | is —CF₂—, —CHF—, —OCF₂—, —OCHF— or a single bond, |
| Y | is F or Cl, |
| a | is 1 or 2, and |
| b | is 0 or 1, | where compounds of the formulae Ib1 to IB4 are excluded from the scope of the formula III.

14. A liquid-crystal display according to claim 3, wherein Component A comprises at least one compound of at least one of the following formulae:

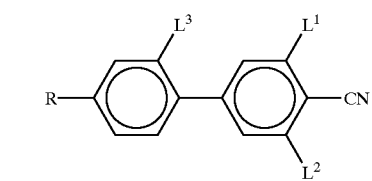

IIa

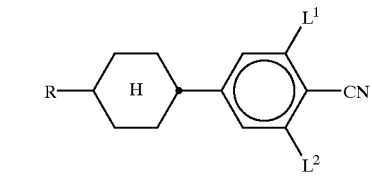

IIb

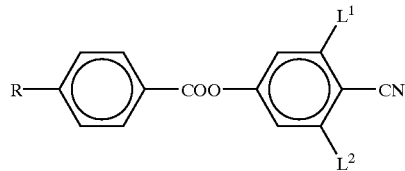

IIc

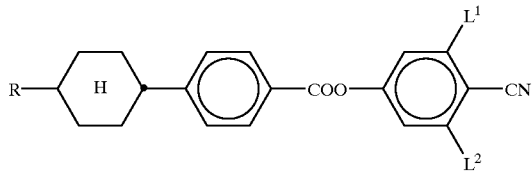

IIf in which R is an alkyl, alkoxy or alkenyl group having 1 to 12 carbon atoms, in which, in addition, one or two non-adjacent CH₂ groups are optionally replaced by —O—, —CH=CH—, —CO—, —OCO— or —COO— in such a way that O atoms are not linked directly to one another, and L¹, L² and L³ are each independently of one another H or F.

15. A liquid-crystal display according to claim 3, wherein Component A comprises one or more compounds of the following formula:

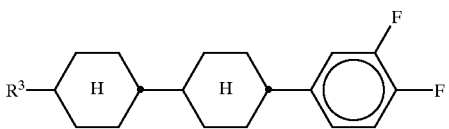

IIIb1 in which R³ is alkyl or alkoxy having 1 to 7 carbon atoms.

16. A liquid-crystal display according to claim 3, wherein Component A comprises one or more compounds of at least one of the following formulae:

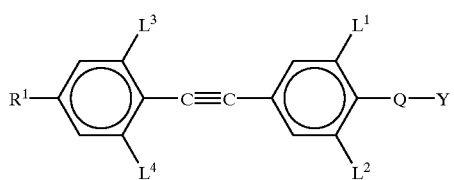

T1a

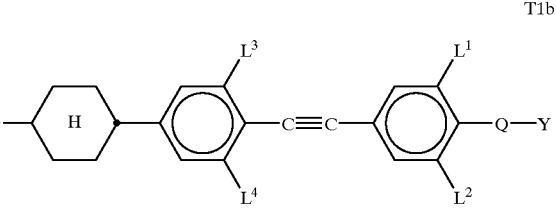

T1b in which L¹ to L⁴ are H or F, Q—Y is F, Cl or OCF₃, and R¹ is an alkyl, alkoxy or alkenyl group having 1 to 12 carbon atoms, in which, in addition, one or two non-adjacent CH₂ groups are optionally replaced by —O—, —CH=CH—, —CO—, —OCO— or —COO— in such a way that O atoms are not linked directly to one another.

17. A liquid-crystal display according to claim 3, wherein Component B comprises one or more compounds selected from the group consisting of compounds of the formulae T2a to T2e:

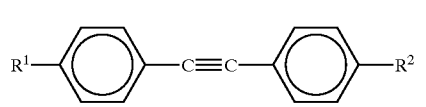

T2a

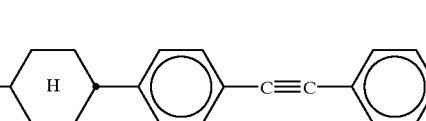

T2b

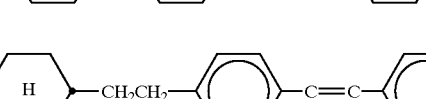

T2c

T2d

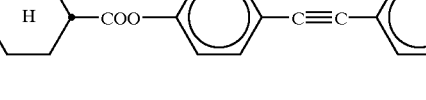

-continued

T2e

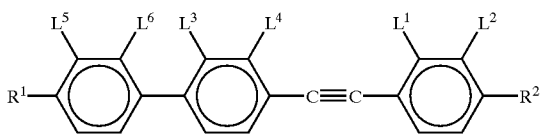

in which $R^1$ and $R^2$ are an alkyl, alkoxy or alkenyl group having 1 to 12 carbon atoms, in which, in addition, one or two non-adjacent $CH_2$ groups are optionally replaced by —O—, —CH=CH—, —CO—, —OCO— or —COO— in such a way that O atoms are not linked directly to one another, and one, two or three of the radicals $L^1$ to $L^6$ are F and the others are H, where $L^1$ and $L^2$ or $L^3$ and $L^4$ or $L^5$ and $L^6$ are not both simultaneously F.

18. A supertwist liquid-crystal display comprising:
two outer plates which, together with a frame, form a cell,
a nematic liquid-crystal mixture of positive dielectric anisotropy which is present in the cell,
electrode layers with alignment layers on the insides of the outer plates,
a pre-tilt angle between the longitudinal axis of the molecules at the surface of the outer plates and the outer plates of from about 0 degrees to 30 degrees, and
a twist angle of the liquid-crystal mixture in the cell from alignment layer to alignment layer with a value of from 22.5° to 600°,
wherein the nematic liquid-crystal mixture comprises:
a) 15–90% by weight of a liquid-crystalline component A consisting of one or more compounds having a dielectric anisotropy of greater than +1.5;
b) 0–60% by weight of a liquid-crystalline component B consisting of one or more compounds having a dielectric anisotropy of between −1.5 and +1.5;
c) 0–20% by weight of a liquid-crystalline component D consisting of one or more compounds having a dielectric anisotropy of below −1.5, and
d) optionally, an optically active component C in such an amount that the ratio between the layer thickness (separation of the outer plates) and the natural pitch of the chiral nematic liquid-crystal mixture is from about 0.2 to 1.3,
wherein the liquid-crystal mixture comprises at least one compound of the formula IA

IA

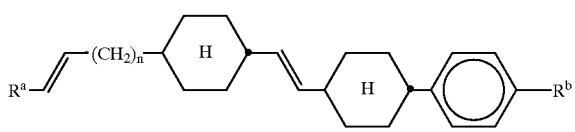

in which

| | |
|---|---|
| $R^a$ | is H or an alkyl group having 1 to 7 carbon atoms, |
| $R^b$ | is an alkyl or alkoxy group having 1 to 10 carbon atoms or an alkenyl or alkenyloxy group having 2 to 10 carbon atoms, |
| and | |
| n | is 0, 1 or 2; | simultaneously comprises at least one compound of the formula IB:

IB

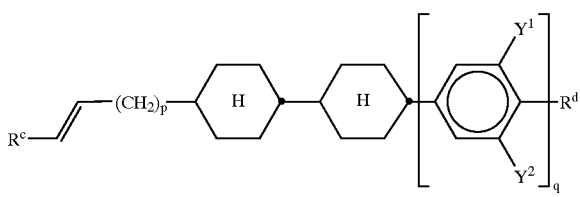

in which

| | |
|---|---|
| $R^c$ | is H or an alkyl group having 1 to 7 carbon atoms, |
| $R^d$ | is F, $OCF_3$, $OCHF_2$, an alkyl or alkoxy group having 1 to 7 carbon atoms or an alkenyl group having 2 to 7 carbon atoms, |
| $Y^1$ and $Y^2$, | independently of one another, are H or F, |
| q | is 0 or 1 |
| and | |
| p | is 0, 1 or 2; and, | wherein Component B comprises one or more compounds selected from the group consisting of compounds of the formulae T3a to T3e:

T3a

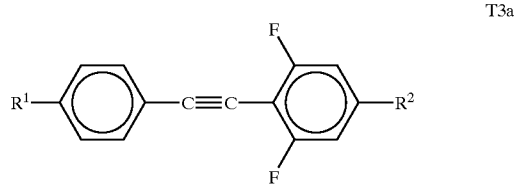

T3b

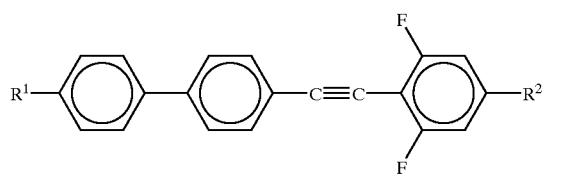

T3c

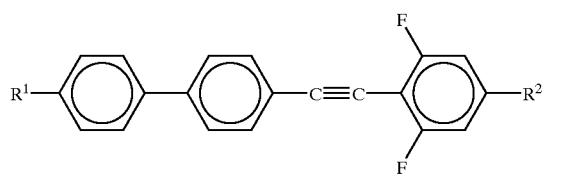

T3d

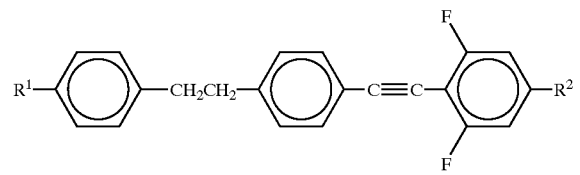

T3e

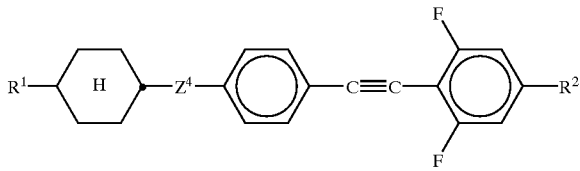

in which $R^1$ and $R^2$ are an alkyl, alkoxy or alkenyl group having 1 to 12 carbon atoms, in which, in addition, one or two non-adjacent CH$_2$ groups are optionally replaced by —O—, —CH=CH—, —CO—, —OCO— or —COO— in such a way that O atoms are not linked directly to one another, and Z$^4$ is —CO—O—, —CH$_2$CH$_2$— or a single bond.

19. A supertwist liquid-crystal display comprising:
two outer plates which, together with a frame, formn a cell,
a nematic liquid-crystal mixture of positive dielectric anisotropy which is present in the cell,
electrode layers with alignment layers on the insides of the outer plates,
a pre-tilt angle between the longitudinal axis of the molecules at the surface of the outer plates and the outer plates of from about 0 degrees to 30 degrees, and
a twist angle of the liquid-crystal mixture in the cell from alignment layer to alignment layer with a value of from 22.5° to 600°,
wherein the nematic liquid-crystal mixture comprises:
a) 15–90% by weight of a liquid-crystalline component A consisting of one or more compounds having a dielectric anisotropy of greater than +1.5;
b) 0–60% by weight of a liquid-crystalline component B consisting of one or more compounds having a dielectric anisotropy of between −1.5 and +1.5;
c) 0–20% by weight of a liquid-crystalline component D consisting of one or more compounds having a dielectric anisotropy of below −1.5, and
d) optionally, an optically active component C in such an amount that the ratio between the layer thickness (separation of the outer plates) and the natural pitch of the chiral nematic liquid-crystal mixture is from about 0.2 to 1.3,
wherein the liquid-crystal mixture comprises at least one compound of the formula IA

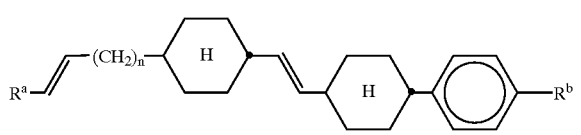

IA in which
R$^a$ is H or an alkyl group having 1 to 7 carbon atoms,
R$^b$ is an alkyl or alkoxy group having 1 to 10 carbon atoms or an alkenyl or alkenyloxy group having 2 to 10 carbon atoms, and
n is 0, 1 or 2;
simultaneously comprises at least one compound of the formula IB:

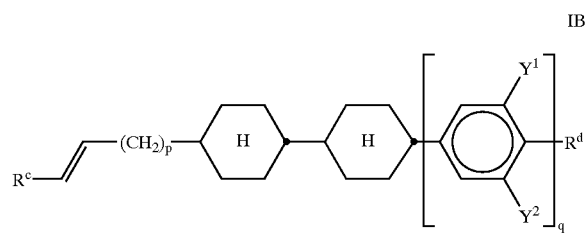

IB in which

| R$^c$ | is H or an alkyl group having 1 to 7 carbon atoms, |
| R$^d$ | is F, OCF$_3$, OCHF$_2$, an alkyl or alkoxy group having 1 to 7 carbon atoms or an alkenyl group having 2 to 7 carbon atoms, |
| Y$^1$ and Y$^2$, | independently of one another, are H or F, |
| q | is 0 or 1 |
| and | |
| p | is 0, 1 or 2; and, | wherein Component B additionally comprises one or more compounds of at least one of the formulae IV25 to IV31:

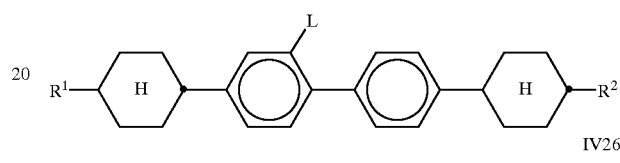

IV25

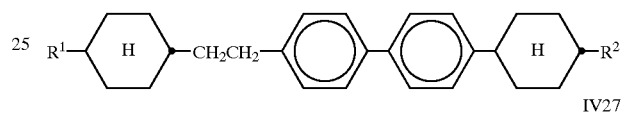

IV26

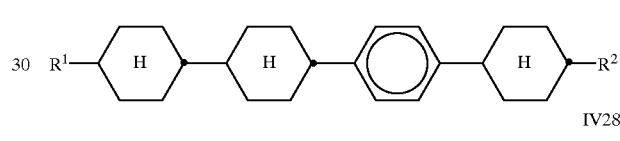

IV27

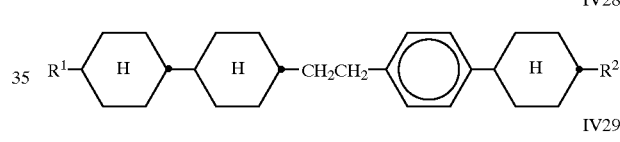

IV28

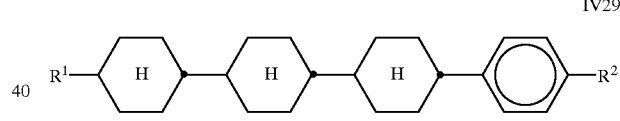

IV29

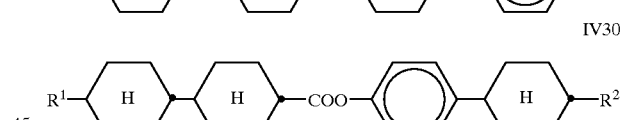

IV30

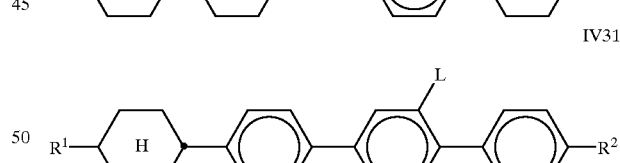

IV31

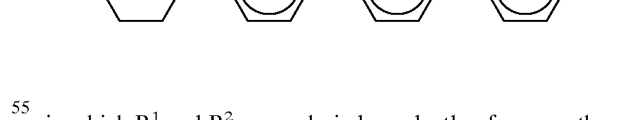

in which R$^1$ and R$^2$ are each, independently of one another, are an alkyl, alkoxy or alkenyl group having 1 to 12 carbon atoms, in which, in addition, one or two non-adjacent CH$_2$ groups are optionally replaced by —O—, —CH=CH—, —CO—, —OCO— or —COO— in such a way that O atoms are not linked directly to one another, and L is H or F.

20. A liquid-crystal display according to claim 18, wherein Component A additionally comprises at least one compound of the formulae II and/or III:

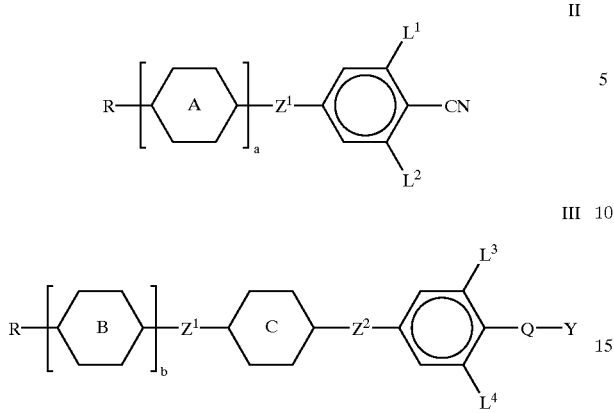

in which

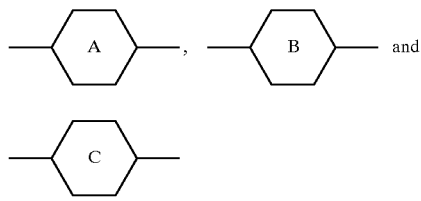

are each, independently of one another

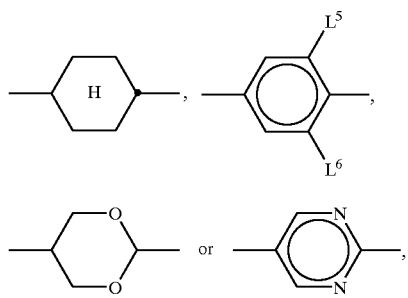

| R | is an alkyl, alkoxy or alkenyl group having 1 to 12 carbon atoms, in which, in addition, one or two non-adjacent CH$_2$ groups are optionally replaced by —O—, —CH=CH—, —CO—, —OCO— or —COO— in such a way that O atoms are not linked directly to one another, |
|---|---|
| L$^1$ to L$^6$ | are each, independently of one another, H or F, |
| Z$^1$ | is —COO—, —CH$_2$CH$_2$— or a single bond, |
| Z$^2$ | is —CH$_2$CH$_2$—, —COO—, —C≡C— or a single bond, |
| Q | is —CF$_2$—, —CHF—, —OCF$_2$—, —OCHF— or a single bond, |
| Y | is F or Cl, |
| a | is 1 or 2, and |
| b | is 0 or 1, | where compounds of the formulae IB are excluded from the scope of the formula III.

21. A liquid-crystal display according to claim 18, wherein Component A comprises at least one compound of at least one of the following formulae:

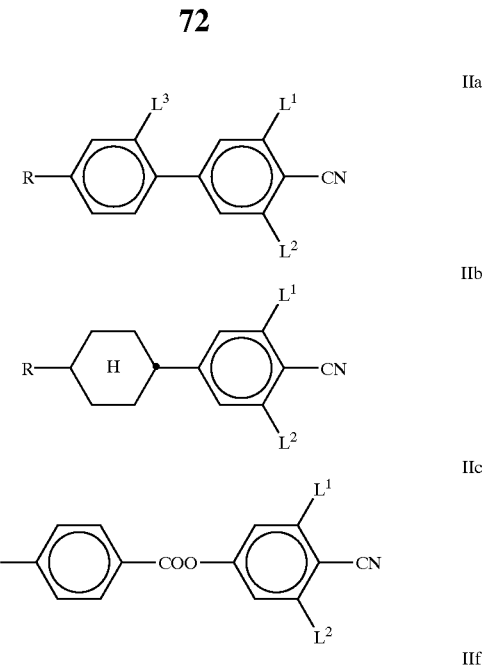

in which R is an alkyl, alkoxy or alkenyl group having 1 to 12 carbon atoms, in which, in addition, one or two non-adjacent CH$_2$ groups are optionally replaced by —O—, —CH=CH—, —CO—, —OCO— or —COO— in such a way that O atoms are not linked directly to one another, and L$^1$, L$^2$ and L$^3$ are each independently of one another H or F.

22. A liquid-crystal display according to claim 18, wherein Component A comprises one or more compounds of the following formula:

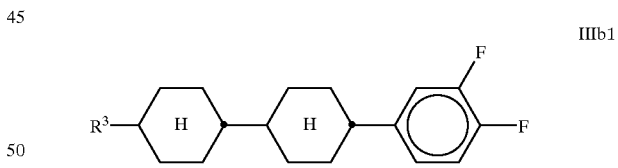

in which R$^3$ is alkyl or alkoxy having 1 to 7 carbon atoms.

23. A liquid-crystal display according to claim 18, wherein Component A comprises one or more compounds of at least one of the following formulae:

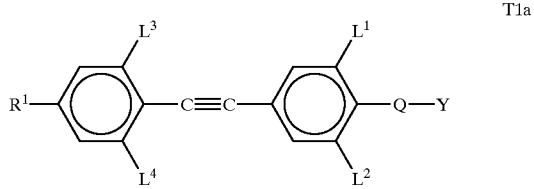

T1b

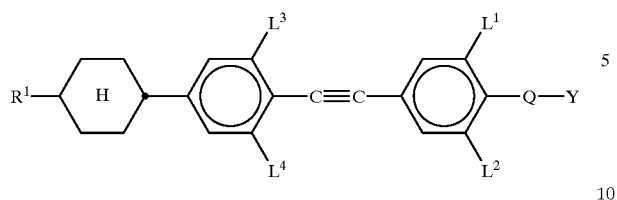

in which L¹ to L⁴ are H or F, Q—Y is F, Cl or OCF₃, and R¹ is an alkyl, alkoxy or alkenyl group having 1 to 12 carbon atoms, in which, in addition, one or two non-adjacent CH₂ groups are optionally replaced by —O—, —CH=CH—, —CO—, —OCO— or —COO— in such a way that O atoms are not linked directly to one another.

24. A liquid-crystal display according to claim 18, wherein Component B comprises one or more compounds selected from the group consisting of compounds of the formulae T2a to T2e:

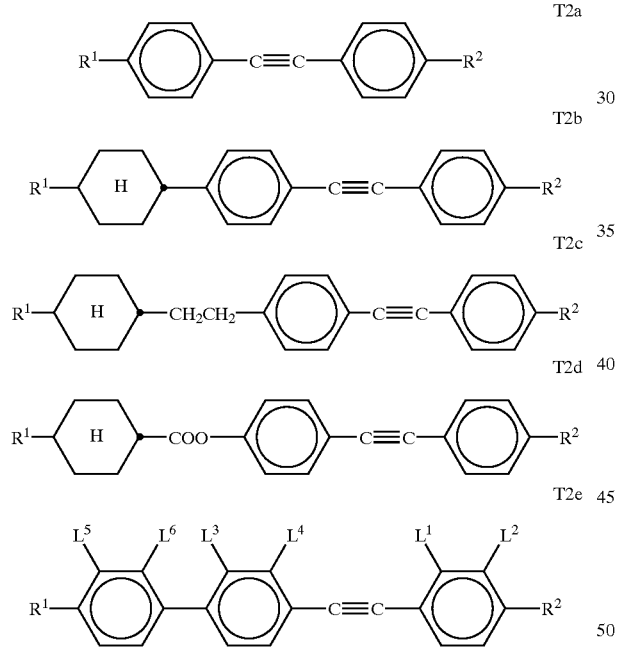

in which R¹ and R² are an alkyl, alkoxy or alkenyl group having 1 to 12 carbon atoms, in which, in addition, one or two non-adjacent CH₂ groups are optionally replaced by —O—, —CH=CH—, —CO—, —OCO— or —COO— in such a way that O atoms are not linked directly to one another, and one, two or three of the radicals L¹ to L⁶ are F and the others are H, where L¹ and L² or L³ and L⁴ or L⁵ and L⁶ are not both simultaneously F.

25. A liquid-crystal display according to claim 19, wherein Component A additionally comprises at least one compound of the formulae II and/or III:

II

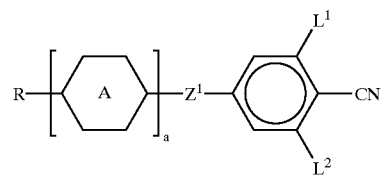

III

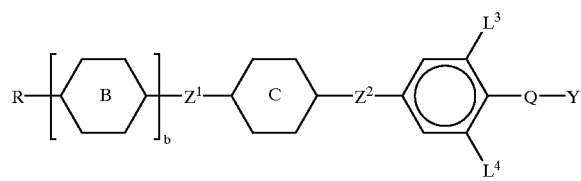

in which

R  is an alkyl, alkoxy or alkenyl group having 1 to 12 carbon atoms, in which, in addition, one or two non-adjacent CH₂ groups are optionally replaced by —O—, —CH=CH—, —CO—, —OCO— or —COO— in such a way that O atoms are not linked directly to one another,

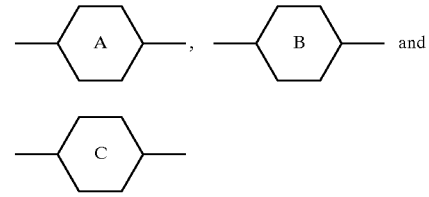

are each, independently of one another

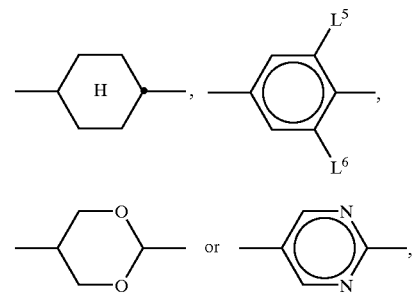

L¹ to L⁶  are each, independently of one another, H or F,
Z¹  is —COO—, —CH₂CH₂— or a single bond,
Z²  is —CH₂CH₂—, —COO—, —C≡C— or a single bond,
Q  is —CF₂—, —CHF—, —OCF₂—, —OCHF— or a single bond,
Y  is F or Cl,
a  is 1 or 2, and
b  is 0 or 1, where compounds of the IB are excluded from the scope of the formula III.

26. A liquid-crystal display according to claim 19, wherein Component A comprises at least one compound of at least one of the following formulae:

IIa

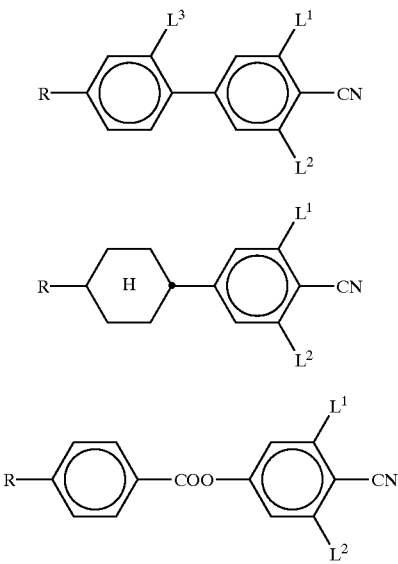

IIb

IIc

IIf

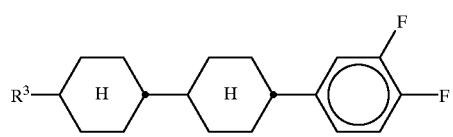

IIIb1

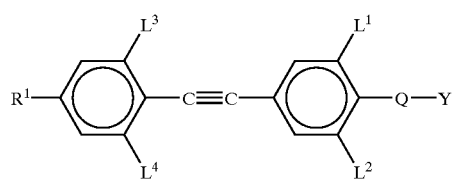

in which R is an alkyl, alkoxy or alkenyl group having 1 to 12 carbon atoms, in which, in addition, one or two non-adjacent CH₂ groups are optionally replaced by —O—, —CH=CH—, —CO—, —OCO— or —COO— in such a way that O atoms are not linked directly to one another, and $L^1$, $L^2$ and $L^3$ are each independently of one another H or F.

27. A liquid-crystal display according to claim 19, wherein Component A comprises one or more compounds of the following formula:

in which $R^3$ is alkyl or alkoxy having 1 to 7 carbon atoms.

28. A liquid-crystal display according to claim 19, wherein Component A comprises one or more compounds of at least one of the following formulae:

T1a

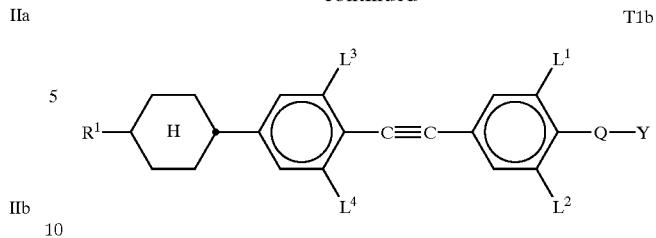

T1b in which $L^1$ to $L^4$ are H or F, Q—Y is F, Cl or OCF₃, and $R^1$ is an alkyl, alkoxy or alkenyl group having 1 to 12 carbon atoms, in which, in addition, one or two non-adjacent CH₂ groups are optionally replaced by —O—, —CH=CH—, —CO—, —OCO— or —COO— in such a way that O atoms are not linked directly to one another.

29. A liquid-crystal display according to claim 19, wherein Component B comprises one or more compounds selected from the group consisting of compounds of the formulae T2a to T2e:

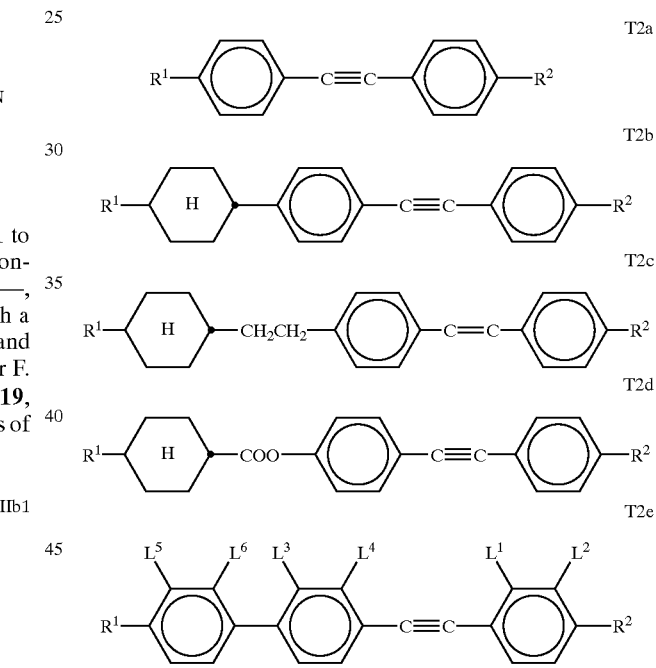

in which $R^1$ and $R^2$ are an alkyl, alkoxy or alkenyl group having 1 to 12 carbon atoms, in which, in addition, one or two non-adjacent CH₂ groups are optionally replaced by —O—, —CH=CH—, —CO—, —OCO— or —COO— in such a way that O atoms are not linked directly to one another, and one, two or three of the radicals $L^1$ to $L^6$ are F and the others are H, where $L^1$ and $L^2$ or $L^3$ and $L^4$ or $L^5$ and $L^6$ are not both simultaneously F.

* * * * *